(12) United States Patent
Lee et al.

(10) Patent No.: US 11,166,952 B2
(45) Date of Patent: Nov. 9, 2021

(54) COMPOSITION INCLUDING RILPIVIRINE AND METHOD FOR TREATING TUMORS OR CANCER

(71) Applicant: Aptorum Therapeutics Limited, Hong Kong (HK)

(72) Inventors: Wai Yip Thomas Lee, Hong Kong (HK); Chung Sing Daniel Poon, Hong Kong (HK); Ka Lun Lai, Hong Kong (HK); Junzhe Huang, Hong Kong (HK); Ho Yin Li, Hong Kong (HK)

(73) Assignee: APTORUM THERAPEUTICS LIMITED, Hong Kong (HK)

( * ) Notice: Subject to any disclaimer, the term of this patent is extended or adjusted under 35 U.S.C. 154(b) by 0 days.

(21) Appl. No.: 17/105,879

(22) Filed: Nov. 27, 2020

(65) Prior Publication Data

US 2021/0161892 A1    Jun. 3, 2021

Related U.S. Application Data

(60) Provisional application No. 63/072,281, filed on Aug. 31, 2020, provisional application No. 62/941,891, filed on Nov. 29, 2019.

(51) Int. Cl.
*A61K 31/505*    (2006.01)
*A61K 45/06*    (2006.01)
*A61P 35/00*    (2006.01)

(52) U.S. Cl.
CPC ............ *A61K 31/505* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | |
|---|---|---|
| 6,838,464 B2 | 1/2005 | Pease et al. |
| 7,067,522 B2 | 6/2006 | Pease et al. |
| 7,125,879 B2 | 10/2006 | Guillemont et al. |
| 7,241,458 B1 | 7/2007 | Verreck et al. |
| 7,638,522 B2 | 12/2009 | Guillemont et al. |
| 7,705,148 B2 | 4/2010 | Schils et al. |
| 7,956,063 B2 | 6/2011 | Guillemont et al. |
| 8,080,551 B2 | 12/2011 | Guillemont et al. |
| 8,101,629 B2 | 1/2012 | Guillemont et al. |
| 8,426,434 B2 | 4/2013 | Stokbroekx et al. |
| 8,841,310 B2 | 9/2014 | Stoffels |
| 9,126,949 B2 | 9/2015 | Reddy et al. |
| 9,139,535 B2 | 9/2015 | Parthasaradhi Reddy et al. |
| 9,233,935 B2 | 1/2016 | Reddy et al. |
| 10,611,732 B2 | 4/2020 | Guillemont et al. |
| 2014/0018379 A1 | 1/2014 | Tung et al. |
| 2014/0349971 A1 | 11/2014 | Stoffels |
| 2015/0283135 A1 | 10/2015 | Stoffels |
| 2017/0100398 A1 | 4/2017 | Stoffels |
| 2020/0069579 A1 | 3/2020 | Patankar et al. |

FOREIGN PATENT DOCUMENTS

| | | |
|---|---|---|
| CN | 100509801 C | 7/2009 |
| CN | 101743006 A | 6/2010 |
| CN | 101060844 B | 1/2012 |
| CN | 105566162 A | 5/2016 |

(Continued)

OTHER PUBLICATIONS

Sciamanna et al. "Inhibition of Endogenous Reverse Transcriptase Antagonizes Human Tumor Growth" *Oncogene*, vol. 24, pp. 3923-3931 (2005).
Liu et al. "Antitumor Activity and Mechanism of a Reverse Transcriptase Inhibitor, Dapivirine, in Glioblastoma" *Journal of Cancer*, vol. 9 No. 1, pp. 117-128 (2018).
Funes et al. "Efavirenz Alters Mitochondrial Respiratory Function in Cultured Neuron and Glial Cell Lines" *Journal of Antimicrobial Chemotherapy*, vol. 70, No. 8, pp. 2249-2254 (2015).
Hecht et al. "Cytotoxic Effect of Efavirenz is Selective Against Cancer Cells and Associated with the Cannabinoid System" *AIDS*, vol. 27, No. 13, pp. 2031-2040 (2013).

(Continued)

*Primary Examiner* — Brian J Davis
(74) *Attorney, Agent, or Firm* — Greenblum & Bernstein, P.L.C.

(57) ABSTRACT

The present invention provides a composition and method for preventing the growth of and/or treating cancerous tumors and/or delaying onset of cancer from tumor-initiating cells. The composition includes an effective amount of a compound of Formula (I) or Formula (II):

or any pharmaceutically acceptable salt thereof. The composition is administered alone or in combination with one or more chemotherapeutic agents, biological agents and/or anticancer agents. The method may include administering the composition of the present invention with or without the chemotherapeutic, biological, or other cancer treatment agent to a subject in need thereof intravenously, parenterally, nasally, topically or locally, orally, or by liposome, implant or via vessel-targeted nanosuspension delivery.

22 Claims, 32 Drawing Sheets

(56) References Cited

FOREIGN PATENT DOCUMENTS

| | | |
|---|---|---|
| CN | 107162987 A | 9/2017 |
| CN | 106187916 B | 8/2018 |
| CN | 109293581 A | 2/2019 |
| EP | 1 419 152 B1 | 7/2011 |
| EP | 2 628 732 A1 | 8/2013 |
| EP | 2 175 857 B1 | 9/2013 |
| EP | 1 663 240 B1 | 4/2015 |
| IN | 2545/CHE/2012 | 3/2014 |
| WO | 03/016306 A1 | 2/2003 |
| WO | 2004/016581 | 2/2004 |
| WO | 2013/087794 A1 | 6/2013 |
| WO | 2013/153161 A3 | 10/2013 |
| WO | 2013/170421 A1 | 11/2013 |
| WO | 2015/136294 A1 | 9/2015 |
| WO | 2019/157087 | 8/2019 |
| WO | 2020/142629 A1 * | 7/2020 ............. A61K 31/33 |

OTHER PUBLICATIONS

Hecht et al. "Efavirenz Has the Highest Anti-Proliferative Effect of Non-Nucleoside Reverse Transcriptase Inhibitors against Pancreatic Cancer Cells" *PLoS ONE*, 10(6):e0130277 (2015).

Landriscina et al. "Reverse Transcriptase Inhibitors Down-Regulate Cell Proliferation in Vitro and in Vivo and Restore Thyrotropin Signaling and Iodine Uptake in Human Thyroid Anaplastic Carcinoma" *The Journal of Clinical Endocrinology & Metabolism*, vol. 90, No. 10, pp. 5663-5671 (2005).

Janssen "EDURANT® Rilpivirine—Australian product information" (2019) www.janssen.com/australia/sites/www_janssen_com_australia/files/prod_files/live/edurant_pi.pdf.

Pittoggi et al. "In Vitro Evidence for a New Therapeutic Approach in Renal Cell Carcinoma" *International Braz. J. Urol*, vol. 34, No. 4, pp. 492-502 (2008).

Tee et al., "Combination Therapy with the CDK7 Inhibitor and the Tyrosine Kinase Inhibitor Exerts Synergistic Anticancer Effects Against MYCN-amplified Neuroblastoma" *Int. J. Cancer*, vol. 147, pp. 1928-1938 (2020).

Nile et al., "An Evaluation In Vitro of PARP-1 Inhibitors, Rucaparib and Olaparib, as Radiosensitisers for the Treatment of Neuroblastoma" *BMC Cancer*, 16:621, pp. 1-13 (2016).

Bhattamisra et al., "Nose to Brain Delivery of Rotigotine Loaded Chitosan Nanoparticles in Human SH-SY5Y Neuroblastoma Cells and Animal Model of Parkinson's Disease" *International Journal of Pharmaceutics*, 579: 119148, pp. 1-11 (2020).

Zareifar et al., "Successful Treatment of Refractory Metastatic Neuroblastoma with Panobinostat in Combination with Chemotherapy Agents and Iodine-131-meta-iodobenzylguanidine Therapy" *J. Oncol. Pharm. Practice*, vol. 0, No. 0, pp. 1-6 (2019).

Kaur et al., "Cytotoxicity of Graphene Oxide (GO) and Graphene Oxide Conjugated Losartan Potassium (GO-LP) on Neuroblastoma (NB41A3) Cells" *J. Nanosci. Nanotechnol.*, vol. 18, pp. 1-11 (2018).

Chen et al., "Small Molecule Inhibitor Regorafenib Inhibits RET Signaling in Neuroblastoma Cells and Effectively Suppresses Tumor Growth In Vivo" *Oncotarget*, vol. 8, No. 61, pp. 104090-104103 (2017).

Taramasso et al., "First-line Antiretroviral Therapy with Efavirenz Plus Tenofovir Disiproxil Fumarate/Emtricitabine or Rilpivirine Plus Tenofovir Disiproxil Fumarate/Emtricitabine: A Duruability Comparison" *HIV Medicine*, vol. 19, pp. 475-484 (2018).

Schlesinger et al., "Establishment and Characterization of Human Neuroblastoma Cell Lines" *Cancer Res.*, vol. 36, pp. 3094-3100 (1976).

Donti et al. "Cytogenetic and Molecular Study of Two Human Neuroblastoma Cell Lines" *Cancer Genet. Cytogenet.*, vol. 30, pp. 225-231 (1988).

Cornaglia-Ferraris et al. "γ-Interferon and Retinoic Acid Synergize in Inhibiting the Growth of Human Neuroblastoma Cells in Nude Mice" *Cancer Letters*, pp. 215-220 (1991).

Ponzoni et al. "Effect of Cytosine Arabinoside on the Growth and Phenotypic Expression of GI-ME-N, a New Human Neuroblastoma Cell Line" *Prog. Clin. Biol. Res.*, vol. 271, pp. 437-448 (1988) (Abstract).

Sekiguchi et al., "Establishment and Characterization of a Human Neuroblastoma Cell Line in Tissue Culture" *Jpn. J. Exp. Med.*, vol. 49, No. 1, pp. 67-83 (1979) (Abstract).

Bettan-Renaud et al., "Potential Therapeutic Role of Cisplatinum in Autologous Bone Marrow Transplantation: In Vitro Eradication of Neuroblastoma Cells from Bone Marrow" *Br. J. Cancer*, vol. 60, pp. 529-532 (1989).

Tumilowicz et al., "Definition of a Continuous Human Cell Line Derived from Neuroblastoma" *Cancer Research*, vol. 30, pp. 2110-2118 (1970).

Seeger et al., "Morphology, Growth, Chromosomal Pattern, and Fibrinolytic Activity of Two New Human Neuroblastoma Cell Lines" *Cancer Research*, vol. 37, pp. 1364-1371 (1977).

Pietsch et al., "Characterization of a Continuous Cell Line (MHH-NB-11) Derived from Advanced Neuroblastoma" *Anticancer Res.*, vol. 8, pp. 1329-1334 (1988).

Gilbert et al., "Abnormalities of Chromosome 1p in Human Neuroblastoma Tumors and Cell Lines" *Cancer Genet. Cytogenet.*, vol. 7, pp. 33-42 (1982).

Carachi et al., "Biological Properties of a Tumour Cell Line (NB1-G) Derived from Human Neuroblastoma" *Br. J. Cancer*, vol. 55, pp. 407-411 (1987).

Foley et al., "Detection Immunohistochemical and Evaluation of Proliferating Cell Nuclear Antigen (PCNA) in Rat Tissue by an Improved Procedure" *Journal of Histotechnology*, vol. 14, No. 4, pp. 237-241 (1991).

Brodeur et al., "Chromosomal Aberrations in Human Neuroblastomas" *Cancer*, vol. 40, pp. 2256-2263 (1977).

Scarpa et al., "Establishment and Characterization of a Human Neuroblastoma Cell Line" *Int. J. Cancer*, vol. 43, No. 4, pp. 645-651 (1989) (Abstract).

Helson et al., "Establishment of a New Cell Line, VA-N-BR, from a Primitive Neuroblastoma Tumor of the Abdomen" *Anticancer Res.*, vol. 12, No. 2, pp. 467-472 (1992) (Abstract).

Biedler et al., "A Novel Chromosome Abnormality in Human Neuroblastoma and Antifolate—Resistant Chinese Hamster Cell Lines in Culture" *JNCI: Journal of the National Cancer Institute*, vol. 57, No. 3, pp. 683-695 (1976) (Abstract).

Biedler et al., "Morphology and Growth, Tumorigenicity, and Cytogenetics of Human Neuroblastoma Cells in Continuous Culture" *Cancer Res.*, vol. 33, pp. 2643-2652 (1973).

Reynolds et al., "Characterization of Human Neuroblastoma Cell Lines Established Before and After Therapy" *JNCI: Journal of the National Cancer Institute*, vol. 76, No. 3, pp. 375-387 (1986) (Abstract).

Whang-Peng et al., "Cytogenetic Characterization of Selected Small Round Cell Tumors of Childhood" *Cancer Genet. Cytogenet.*, vol. 21, pp. 185-208(1986).

Bagnara et al., "Establishment and Characterization of a Primitive Neuroectodermal Tumor of Bone Continuous Cell Line (LAP-35)" *International Journal of Cell Cloning*, vol. 8, pp. 409-424 (1990).

Yeger et al., "Importance of Phenotypic and Molecular Characterization for Identification of a Neuroepithelioma Tumor Cell Line, NUB-20" *Cancer Res.*, vol. 50, pp. 2794-2802 (1990).

Cavazzana et al., Olfactory Neuroblastoma is Not a Neuroblastoma But is Related to Primitive Neuroectodermal Tumor (PNET), *Prog. Clin. Biol. Res.*, vol. 271, pp. 463-473 (1988) (bibliographic information).

Rostomily et al., "Expression of Neurogenic Basic Helix-Loop-Helix Genes in Primitive Neuroectodermal Tumors" *Cancer Res.*, vol. 57, pp. 3526-3531 (1997).

Maestrini et al., A Family of Transmembrane Proteins with Homology to the MET-Hepatocyte Growth Factor Receptor, *Proc. Natl. Acad. Sci. USA*, vol. 93, pp. 674-678 (1996).

Pozniak et al., "Efficacy and Safety of TMC278 in Antiretroviral-naive HIV-1 Patients: Week 96 Results of a Phase IIb Randomized Trial" *AIDS*, vol. 24, pp. 55-65 (2010).

International Search Report issued in PCT/CN2020/132422 dated Mar. 8, 2021.

Written Opinion issued in PCT/CN2020/132422 dated Mar. 8, 2021.

* cited by examiner

COMPOSITION INCLUDING RILPIVIRINE AND METHOD FOR TREATING TUMORS OR CANCER

CROSS-REFERENCE TO RELATED APPLICATIONS

The present application claims the benefit under 35 U.S.C. § 119(e) of U.S. Provisional Application Nos. 62/941,891, filed Nov. 29, 2019, and 63/072,281, filed Aug. 31, 2020, the disclosures of each of which are incorporated herein by reference in their entireties.

FIELD OF THE INVENTION

The present invention relates to a composition comprising rilpivirine for cancer treatment as well as treatment of precancerous conditions. In particular, the composition is administered alone or in combination with one or more therapeutic agents comprising one or more of chemotherapeutic, biological and/or anticancer agents to a subject in need thereof.

BACKGROUND

Cancer is a complex disease which is usually caused by specific changes to the genes in one cell or group of cells and leads to disruption in normal cell function. There are at least six major differences between normal cells and cancer cells. (A) Growth: normal cells stop growing when sufficient cells are present. However, cancer cells do not stop growing and divide more quickly than normal cells; this uncontrolled cell growth may result in the formation of a tumor. (B) Cell repair and cell death: normal cells are either repaired or experience programmed cell death when they are damaged or older (apoptosis). In contrast, cancer cells are either not repaired or do not undergo apoptosis. (C) Metastasis: normal cells stay in the region of the body where they belong; however, cancer cells migrate and invade other tissues or organs via the bloodstream and the lymphatic system. (D) Appearance: normal cells have a regular, ordered appearance; in contrast cancer cells are misshapen, and appear as a chaotic collection of cells, in an array of shapes and sizes. (E) Maturation: normal cells usually differentiate into mature cells and functionalize naturally; however cancer cells grow and divide rapidly and stay in an undifferentiated state. (F) Genomic stability: normal cells have standard DNA and chromosome numbers; however, the chromosomes of cancer cells often have abnormal numbers of chromosome and cancer cells' DNA may become increasingly abnormal as it accumulates mutations.

There are various approaches to cancer treatment. For many types of cancer, chemotherapy is one of the most common and conventional treatments. In general, it involves administration of cytotoxic agents to destroy cancer cells or stop them from growing/dividing and migrating to other parts of the body. More than 100 chemotherapy agents are used for cancer treatment. There are several different classes of drugs employed during cancer treatment including: (a) alkylating agents which prevent the cells from reproducing by damaging their DNA in all phases of cell cycles; (b) anti-metabolites which interfere with the replication of DNA and RNA by substituting for the normal building blocks of DNA and RNA; (c) antibiotics which inhibit the enzymes for DNA replication; (d) topoisomerase inhibitors which inhibit enzymes for unwinding strands of DNA during replication and transcription, i.e., topoisomerase I or topoisomerase II; (e) mitotic inhibitors which inhibit mitosis and cell division; and (f) corticosteroids which are used for relieve the side effect caused by other drugs.

Chemotherapeutic agents inhibit the growth of cells including both cancer cells and normal cells; these normal cells include new blood cells in the bone marrow, epithelial cells in the mouth, stomach, skin, hair, or reproductive organs in the body. This is the major limitation or disadvantage of chemotherapy: it is unable to differentiate between normal and abnormal cells in the body. Therefore, patients often experience serious side effects during and after chemotherapy treatment.

The anti-proliferative effects of non-nucleoside reverse transcriptase inhibitors (NNRTIs) have been the subject of various studies. For example, certain reverse transcriptase inhibitors such as nevirapine and efavirenz have been shown to antagonize tumorigenic growth of A-375 melanoma and PC3 prostate cancer cell lines in animal experiments (*Oncogene* 24:3923-3931, 2005). Dapivirine has been shown to inhibit tumor growth of U87 glioblastoma cells (*Journal of Cancer* 9(1):117-128, 2018). In vitro efavirenz and rilpivirine (a second generation NNRTI approved by FDA for the treatment of HIV infection) have been found to have high toxic potential against pancreatic cancer cells (*PloS ONE* 10(6):e0130277, 2015). However, there remains a need for developing new cancer treatments, particularly those that are well-tolerated and have fewer serious side effects. More specifically, there remains a need for additional medicines that function safely, effectively, and/or synergistically in combination with other anticancer treatments, as well as a need for cancer treatments that may be safe and effective without additional chemotherapeutic agents.

SUMMARY OF THE INVENTION

The present invention is not to be limited in scope by any of the following descriptions. The following examples or embodiments are presented for exemplification only.

The term "cancer" not only refers to solid tumors, such as cancers of the breast, respiratory tract, brain, nerve tissue, reproductive organs, digestive tract, urinary tract, eye, liver, skin, head and neck, thyroid, parathyroid, and their distant metastases, but also blood cancers including but not limited to lymphomas, sarcomas, and leukemias.

Breast cancers include, but are not limited to invasive ductal carcinoma, invasive lobular carcinoma, ductal carcinoma in situ, and lobular carcinoma in situ.

Respiratory tract cancers include, but are not limited to small-cell and non-small-cell lung carcinoma, as well as bronchial adenoma and pleuropulmonary blastoma.

Brain cancers include, but are not limited to brain stem and hypothalamic glioma, cerebellar and cerebral astrocytoma, glioblastoma, medulloblastoma, ependymoma, as well as neuroectodermal and pineal tumor.

Eye cancers include, but are not limited to intraocular melanoma and retinoblastoma.

Liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, fibrosarcoma, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

Nerve tissue related tumor include, but are not limited to neuroblastoma, ganglioneuroblastoma, ganglioneuroma, schwannomas, or neurofibrosarcomas.

Male reproductive organ tumors include, but are not limited to prostate and testicular cancer.

Female reproductive organ tumors include, but are not limited to endometrial, cervical, ovarian, vaginal, and vulvar cancer, as well as sarcoma of the uterus.

Digestive tract tumors include, but are not limited to anal, colon, colorectal, esophageal, gallbladder, gastric, pancreatic, rectal, small intestine, and salivary gland cancers.

Urinary tract tumors include, but are not limited to bladder, penile, kidney, renal pelvis, ureter, and urethral cancers.

"Precancerous conditions" as used herein, relate to abnormal cells that have an increased risk of turning cancerous.

Above diseases have been well characterized in humans, and can be treated by administering one or more therapeutic agents of the present invention.

A pharmaceutically acceptable excipient is any excipient which is relatively non-toxic and innocuous to a patient at concentrations consistent with effective activity of the active ingredient so that any side effects ascribable to the excipient do not vitiate the beneficial effects of the active ingredient.

One aspect of the present invention provides a composition for inhibiting growth of and/or treating a cancerous tumor and/or delaying onset of cancer from tumor-initiating cells, the composition comprising:

an effective amount of a compound of Formula (I) or Formula (II):

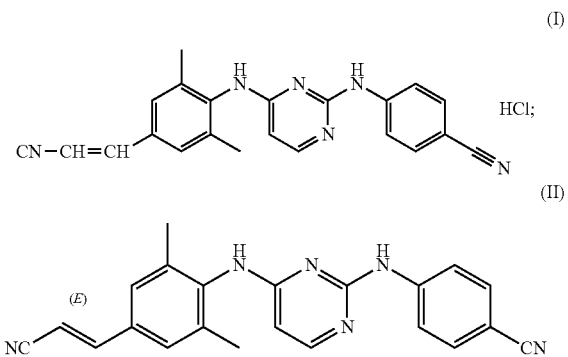

or any pharmaceutically acceptable salt thereof, said composition being administered alone or in combination with one or more of the following chemotherapeutic agents, biological agents and/or anticancer agents ("therapeutic agents" is used interchangeably hereinafter) to a subject in need thereof.

In one aspect, the one or more chemotherapeutic agents may be alkylating agents, anti-metabolites, antitumor antibiotics, topoisomerase inhibitors, kinase inhibitors, mitotic inhibitors, steroids and/or any mixtures thereof.

The one or more biological agents may include but are not limited to vaccines, cytokines, antibodies, protein and peptide drugs, and/or any mixtures thereof. The treatment with rilpivirine may also be combined with other cancer treatments such as radiation treatment, T-cell therapy, etc.

In one embodiment, the composition of the present invention can be combined with anti-cancer agents including, but not limited to asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

In one embodiment, the composition of the present invention can be combined with other cytotoxic drugs including, but not limited to aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxy-uridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, vinorelbine, xaliplatin, gemcitabine, capecitabine, epothilone and its natural or synthetic derivatives, temozolomide, tositumomab (Bexxar), trabedectin, and the inhibitors of the kinesin spindle protein Eg5.

The composition of the present invention can be combined with anticancer agents, including but not limited to Tyrosine Kinase Inhibitors (TKI), as well as signal transduction inhibitors which target the EGFR family and their related ligands including, but not limited to Herceptin (trastuzumab), Erbitux (cetuximab), pertuzumab, ZD-1839/Iressa, OSI-774/Tarceva, CI-1033, GW-2016, CP-724,714, HKI-272, and EKB-569.

In one embodiment, the composition of the present invention can be combined with inhibitors of the Raf/MEK/ERK transduction pathway including, but not limited to PD-325901, and ARRY-142886.

In one embodiment, the composition of the present invention can be combined with inhibitors targeting the protein site of Rho-associated protein kinase 2 (ROCK2) including, but not limited to Lapatinib, Paroxetine, Rucaparib, Doxepin, Levobunolol, Darifenacin, Risperidone, Frovatriptan, Rotigotine, Rotigotine, Carteolol, Ipratropium, Testosterone, Danazol, and derivatives thereof.

In one embodiment, the composition need of the present invention can be combined with inhibitors targeting the protein site of Aurora A including, but not limited to Ziprasidone, Methyltestosterone, Exemestane, Panobinostat, Dolasetron, Letrozole, Lapatinib, Lenvatinib, Losartan, Axitinib, Flavoxate, Irbesartan, Nintedanib, Dibucaine, Iloperidone, Erlotinib, Paliperidone, Alprazolam, Halcion, Regorafenib, and derivatives thereof.

In one embodiment, the composition of the present invention can be combined with inhibitors targeting the protein site of Bromodomain-containing protein 4 (BRD4) including, but not limited to Nicardipine, Alfentanil, cilostazol, Alfuzosin, Pomalyst, Vemurafenib, Losartan, Salmeterol, Nebivolol, Podofilox, Midazolam, and derivatives thereof.

In one embodiment, the composition of the present invention can be combined with proteasome inhibitors and mTOR inhibitors including, but not limited to bortezomib and CCI-779.

In one embodiment, the composition of the present invention can be combined with biological therapies including, but not limited to immunotherapy (such as vaccines, cytokines, and some antibodies), gene therapy, and some targeted therapies.

In one embodiment, the composition of the present invention can be combined with cytokines including, but not limited to IL-2 or an interferon (IFN), and optionally the interferon is an alpha-IFN or a gamma-IFN; and optionally the IL-2 is a recombinant IL-2.

In one embodiment, the composition of the present invention can be combined with monoclonal antibody against GD2 protein including, but not limited to Hu3F8, hu14.18K322A, Hu14.18-IL-2, and dinutuximab (Qarziba).

In embodiments, the preferable dosage of rilpivirine is from about 0.1 mg to 1000 mg, and more preferably from 1 mg to 25 mg. For example, it may be administered to the subject at a dosage of 1, 2, 3, 4, 5, 6, 7, 8, 9, 10, 11, 12, 13, 14, 15, 16, 17, 18, 19, 20, 21, 22, 23, 24, or 25 mg per day.

Another aspect of the present invention provides a method for preventing growth of and/or treating cancerous tumors and/or delaying onset of cancer from tumor-initiating cells, comprising administering a composition comprising an effective amount of the compound of Formula (I) or Formula (II):

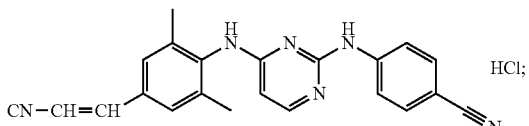

(I)

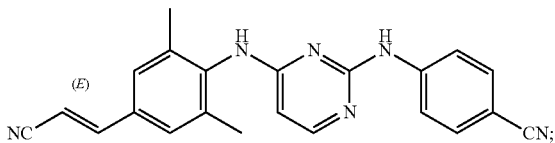

(II)

or any pharmaceutically acceptable salt thereof, to a subject in need thereof.

In an embodiment, the composition may be administered alone or in combination with one or more chemotherapeutic, biological, and/or anticancer agents to the subject in need thereof.

In an embodiment, such a method is contemplated wherein the one or more chemotherapeutic agents comprise one or more alkylating agents, anti-metabolites, antitumor antibiotics, topoisomerase inhibitors, mitotic inhibitors, steroids, and/or any mixtures thereof; and the one more biological agents comprise one or more of vaccines, cytokines, antibodies, protein and peptide drugs and/or any mixtures thereof.

In an embodiment, the one or more alkylating agents for the method are one or more selected from cyclophosphamide, melphalan, temozolomide, carboplatin, cisplatin, and/or oxaliplatin.

In an embodiment, the one or more anti-metabolites are one or more selected from 5-fluorouracil, 6-mercaptopurine, cytarabine, gemcitabine, and/or methotrexate.

In an embodiment, the one or more antitumor antibiotics are one or more selected from actinomycin-D, bleomycin, daunorubicin, and/or doxorubicin.

In an embodiment, the one or more topoisomerase inhibitors are one or more selected from etoposide, irinotecan, teniposide, and/or topotecan.

In an embodiment, the one or more mitotic inhibitors are one or more selected from docetaxel, estramustine, paclitaxel, and/or vinblastine.

In an embodiment, the one or more steroids are one or more selected from prednisone, methylprednisolone, and/or dexamethasone.

In an embodiment, the one or more antibodies are selected from Hu3F8, hu14.18K322A, Hu14.18-IL-2, dinutuximab, or any combination thereof.

In an exemplary embodiment, the compound of Formula (I) or (II) and/or the pharmaceutically acceptable salt thereof, in the composition targets tumor-initiating cells capable of growing or developing into neuroblastoma in the subject.

As used herein, the term "prevent" or "prevention" in the context of treatment, for example, as in "preventing cancer" or "preventing the growth of cancer" refers to a reduction in cancer. Prevention does not require 100% elimination of the symptom.

In one embodiment, said composition is formulated into one or more of the following administrative forms: a parenteral formulation, an aqueous solution, a liposome, an injectable solution, suspension or emulsion, an intravenous solution, a tablet, a pill, a lozenge, a capsule, a caplet, a patch, a spray, an inhalant, a powder, a freeze-dried powder, an inhalant, a patch, a gel, a geltab, a nanosuspension, a nanoparticle, a nanoliposome, a microgel, a pellet, a suppository, an oral suspension, an oral disintegrating tablet, a dispersible tablet, an oral disintegrating film, a microemulsion, a nanoemulsion, and a self-emulsifying drug delivery system, and/or any combination thereof.

In embodiments, said cancerous tumor or cancer comprises a mastocytoma or a mast cell tumor, an ovarian cancer, a non-small cell lung cancer, small cell lung cancer, hepatocarcinoma, melanoma, retinoblastoma, breast tumor, colorectal carcinoma, leukemia, lymphoma, acute lymphoblastic leukemia (ALL) or acute lymphoid leukemia, acute myeloid leukemia (AML), a histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer.

In a preferred embodiment, said cancerous tumor or cancer comprises neuroblastoma. In an exemplary embodiment, the cancerous tumor or cancer is developed from neuroblastoma-initiating cells in the subject. In other words, the compounds of Formula (I) or (II) and/or the pharmaceutically acceptable salt thereof in the present composition is for targeting and inhibiting the proliferation of tumor-initiating cells which are capable of developing into neuroblastoma in the subject.

In embodiments, said subject is human comprising adult, juvenile, children and infants. In an exemplary embodiment, the subject may be one having neuroblastoma, diagnosed with neuroblastoma, at recognized risk of having neuroblastoma, or in recognized need of neuroblastoma treatment. In embodiments, the subject may be one having or diagnosed with one of the other cancers contemplated herein, or at recognized risk of having one of the other cancers contemplated herein or in recognized need of cancer treatment.

In embodiments, the composition is administered intravenously, parenterally, intramuscularly, subcutaneously, nasally, pulmonarily, topically or locally, orally, buccally, sublingually, vaginally, rectally, instillation, injection, implantation into the eyes, surgical implantation, or by liposome, implant or via vessel-targeted nanosuspension delivery to said subject.

In embodiments, the effective amount of said compound in the composition is from about 0.1 mg to 1000 mg per day, and more preferably the effective amount of said compound in the composition is from 0.1 mg to 25 mg per day. For example, the compound in the composition is administered to the subject in an effective amount of 1, 2, 3, 4, 5, 6, 7, 8, 9, 10, 11, 12, 13, 14, 15, 16, 17, 18, 19, 20, 21, 22, 23, 24 or 25 mg per day.

In embodiments, the composition is administered at least once daily, for example, once per day, twice per day, three times per day, four times per day, etc.

The candidates for each of the agents described herein should be understood to be applicable to or combinable with the present composition in any of the aspects of the present invention.

Another embodiment relates to a method for reducing the frequency or amount of a chemotherapeutic agent needed to treat cancerous tumors and/or delay progression of cancer from tumor-initiating cells, the method comprising administering a composition comprising an effective amount of a compound of Formula (I) or Formula (II):

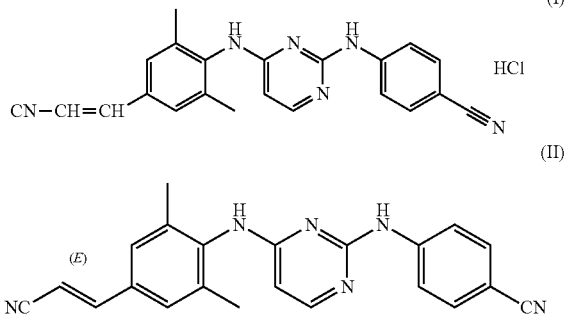

or any pharmaceutically acceptable salt thereof, in combination with one or more of chemotherapeutic agents, to a subject in need thereof, the one or more of the chemotherapeutic agents being selected from alkylating agents, antimetabolites, antitumor antibiotics, topoisomerase inhibitors, mitotic inhibitors, steroids and/or any mixtures thereof; wherein the frequency or amount of the chemotherapeutic agent administered is approximately up to 75 to 90 percent less than a standard protocol without administration of the composition comprising an effective amount of the compound of Formula (I) or Formula (II).

BRIEF DESCRIPTION OF THE DRAWINGS

Embodiments of the present invention are described in more detail hereinafter with reference to the drawings.

FIG. 1A is the control group and shows IMR-32 cells incubated for 24 h without drug treatment; FIG. 1B shows IMR-32 cells treated with rilpivirine (5 μM) for 24 h FIG. 1C shows the percentage cell viability of IMR-32 treated (72 h) with various concentrations of rilpivirine.

DETAILED DESCRIPTION

Figure 1A:
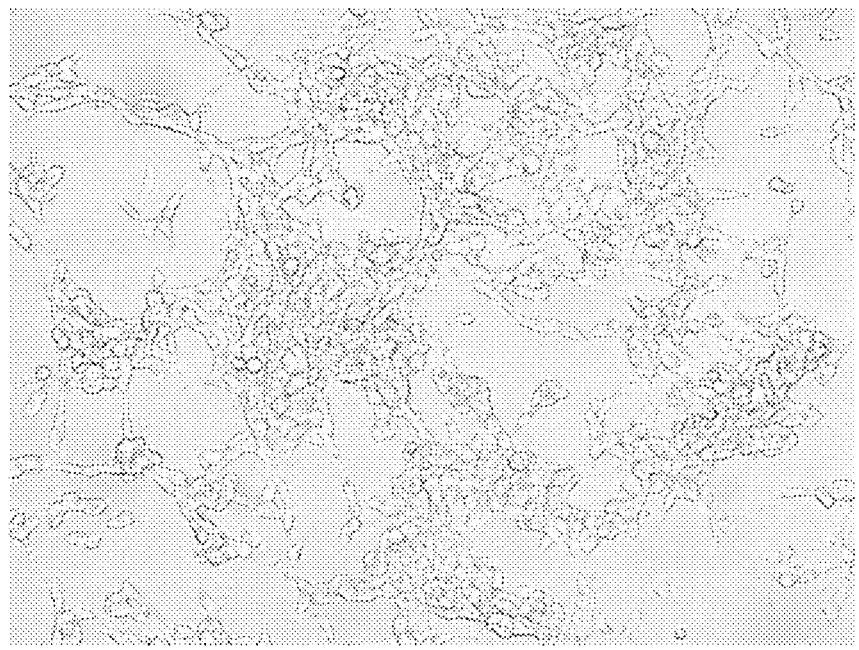
FIG. 1A, FIG. 1B, and FIG. 1C illustrate the inhibition of the neuroblastoma cells IMR-32 under the treatment of rilpivirine alone.

The present invention relates to the use of rilpivirine, its base form, or salts thereof, alone or in combination with other cancer therapies, to treat cancer, while minimizing serious side effects from those other cancer therapies. Prevention of the genesis of cancer, as well as the substantial reduction or elimination of malignant cells and/or symptoms associated with the development and metastasis of malignancies are contemplated. The treatment of precancerous conditions is also contemplated herein.

Compounds of Formula I or II, shown below, may be employed in the present invention:

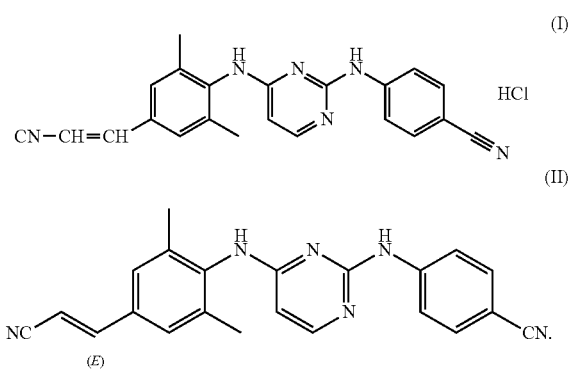

The compounds of Formula II are generally referred to as a "base" form of rilpivirine. Pharmaceutically acceptable salts of the Formula II compound may also be used, including, but not limited to, phosphates, acetates, maleates, and sulfates thereof. The forms may be crystalline or amorphous.

In the present invention, rilpivirine of Formula (I), (II), or its salts is used alone or is combined with various anti-cancer agents, biological agents, or other treatments in order to treat a variety of cancers. The addition of rilpivirine to a chemotherapy regime or chemotherapeutic agent permits a substantial reduction in the amount of the chemotherapeutic agent needed to reduce tumor sizes, thereby greatly diminishing the harmful side-effects of those chemotherapeutic agents. In some aspects, the amount of chemotherapeutic agent or biologic agent reduction may be up to 75 to 90 percent of the amount and or frequency of the standard treatment regimen.

In one aspect, the invention includes a method for preventing growth of and/or treating cancerous tumor and/or delaying onset of cancer from tumor-initiating cells, by administering a composition comprising an effective amount of a compound of Formula (I) or Formula (II):

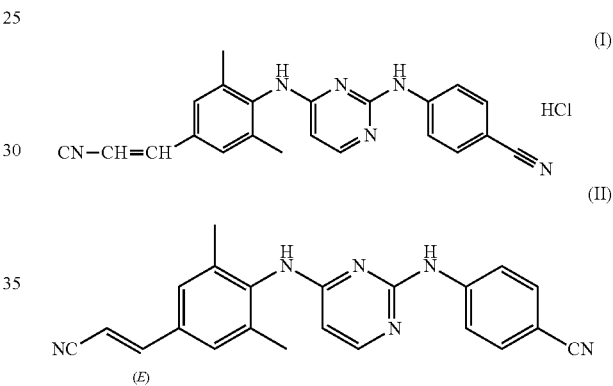

Alternatively, a pharmaceutically acceptable salt of the compound of Formula (II) may be used. The compound of Formula (I) or Formula (II) is administered alone or in combination with one or more chemotherapeutic, biological and/or anticancer agents. By "in combination," it is meant that the composition of Formula (I) or Formula (II) may be administered separately, at the same time in synchrony, or by chrono-dosing, concurrent infusion or separate infusion with the one or more of the chemotherapeutic, biological and/or anticancer agents, and wherein one of the chemotherapeutic, biological and/or anticancer agents can be administered before or after the other.

The composition may be administered intravenously, parenterally, nasally, topically or locally, orally, or by liposome, implant or via vessel-targeted nanosuspension delivery to the subject.

While not being bound by theory, it is believed that the compounds of Formula (I) or (II) may disrupt cancer cell replication by interfering with DNA replication. Thus, rilpivirine may increase DNA damage, reduce the DNA repair mechanism, degrade MYCN, and/or inhibit angiogenesis. Further, the compounds of Formula (I) or (II) may shut down survival signals by kinase inhibition. Alternatively, the compounds of Formula (I) or (II) may increase the uptake by the targeted tumor cells of chemotherapeutic drugs by interfering with the efflux transporters such a p-glycoprotein and BCRP.

The chemotherapeutic agent may be one or more of alkylating agents, anti-metabolites, antitumor antibiotics, topoisomerase inhibitors, mitotic inhibitors, steroids and/or any mixtures thereof The alkylating agents may be one or more of cyclophosphamide, melphalan, temozolomide, carboplatin, cisplatin, and/or oxaliplatin. The anti-metabolites may be one or more of from 5-fluorouracil, 6-mercaptopurine, cytarabine, gemcitabine, and/or methotrexate. The antitumor antibiotics may be one or more of actinomycin-D, bleomycin, daunorubicin, and/or doxorubicin. The topoisomerase inhibitors may be one or more of etoposide, irinotecan, teniposide, and/or topotecan. The mitotic inhibitors may be one or more of docetaxel, estramustine, paclitaxel, and/or vinblastine. The steroids may be one or more of prednisone, methylprednisolone, and/or dexamethasone.

The method of the present invention may be used to treat a variety of cancers. In one aspect a cancerous tumor or cancer may be a mastocytoma or a mast cell tumor, an ovarian cancer, pancreatic cancer, a non-small cell lung cancer, small cell lung cancer, hepatocarcinoma, melanoma, retinoblastoma, breast tumor, colorectal carcinoma, leukemia, lymphoma, acute lymphoblastic leukemia (ALL) or acute lymphoid leukemia, acute myeloid leukemia (AML), a histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer.

The treatment of the present invention is intended to apply to humans including adults, juveniles, children and infants.

An effective amount of the compound in the composition is from about 0.1 mg to 1000 mg per day. As is understood by those in the art, the dosing may vary based on the type of cancer, the stage of the cancer, the method of administration, and the amount and type of the co-administered chemotherapeutic or biological agent. In another aspect, the range of the compound amount is from 0.1 mg to 25 mg per day. For example, the compound in the composition is administered to the subject in an effective amount of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25 mg per day.

The administration time period may be one or more times per day, several times per week, or once per week or multiple weeks, depending on other treatments being performed and the type and stage of the cancer.

The biological agent may be one or more of vaccines, cytokines, antibodies, protein and peptide drugs and/or any mixtures thereof. The antibodies may be one or more of Hu3F8, hu14.18K322A, Hu14.18-IL-2, dinutuximab or any combination thereof. In one aspect two or more chemotherapeutic, biological and/or other anticancer agents are formulated with said compound of Formula (I) or (II) for administration to a subject.

The compound of Formula (I) or (II) may be formulated into one or more of the following administrative forms: a parenteral formulation, an aqueous solution, a liposome, an injectable solution, an injectable suspension, an injectable emulsion, an intravenous solution, an intravenous suspension/nanosuspension, a tablet, a pill, a lozenge, a capsule, a caplet, a patch, a spray, an inhalant, a powder, a freeze-dried powder, a patch, a gel, a geltab, a suspension, a nanosuspension, a microparticle, a nanoparticle, a nanoliposome, a microgel, a pellet, a suppository, an oral suspension, an oral disintegrating tablet, an oral dispersible tablet, an oral disintegrating film, a microemulsion, a nanoemulsion and a self-emulsifying drug delivery system and/or any combination thereof Initially, isobologram and combination index analysis were performed to evaluate the drug-drug interaction between rilpivirine (RPV) and other potential chemotherapeutic agents. Isobologram analysis evaluates the interaction between two drugs at a given effect level. The drug-drug interaction between rilpivirine and other chemotherapeutic agents was analyzed against neuroblastoma cell lines such as CHP-100, CHP-126, CHP-134B, CHP-212, CHP-234, CHP-382, CHP-404 (Schlesinger et al., 1976), GI-CA-N (Donti et al., 1988), GI-LI-N (Cornaglia et al., 1992), GI-ME-N (Ponzoni et al., 1988), GOTO (Sekiguichi et al., 1979), IGR-N-835 (Bettan et al., 1989), IMR-32 (Tumilocwicz et al., 1970), LA-N-1, LA-N-5 (Seeger et al., 1977), MHH-NB11 (Pietsch et al., 1988), NB-69 (Gilbert et al., 1982), NB1-G (Carachi et al., 1987), NBL-W (Foley et al., 1991), NGP, NGP-2, NLF, NMB (Brodeur et al., 1977), RN-GA (Scarpa et al., 1989), SK-N-AS, SK-N-DZ, SK-N-FI, SK-N-LE, SK-PN-LO, SK-PN-LI, SK-PN-DW, VA-N-BR (Helson and Helson, 1985), SK-N-BE(2) (Biedler and Spengler, 1976), SK-N-SH (Biedler et al., 1983), SMS-KAN, SMS-KANR, SMS-KCN, SMS-KCNR (Reynolds et al., 1986), TC-32, TC-106, N1000, N1008, N1016, A4573 (Whang-Peng et al., 1986), LAP-35 (Bagnara et al., 1990), NUB-20 (Yeger et al., 1990), SK-N-MC (Biedler et al., 1983), and TC-268 (Cavazzana et al, 1988); all of which of incorporated herein by reference in their entireties.

Neuroblastoma Cell Lines

IMR-32 cell line is a human neuroblastoma cell line established from an abdominal mass in a 13-month-old Caucasian male (Tumilocwicz et al., 1970; Rostomily R C, et al., 1997; Maestrini E, et al. 1996), and has been widely used as a model for neural related disease. In addition to IMR-32 cell line, the growth of three additional neuroblastoma cell lines (SK-N-BE(2), SK-N-SH, and SH-SY5Y) were also successfully inhibited under rilpivirine treatment.

Isobologram Analysis

In the present invention, the $IC_{50}$ concentrations required to inhibit the activity of IMR-32 cell line and other neuroblastoma cell lines were determined for rilpivirine and other chemotherapeutic agents, and presented on the two-coordinate plot with x- and y-axes, forming the two points $(IC_{50, rilpivirine}, 0)$ and $(0, IC_{50, chemotherapeutic agents})$. The line connecting these two points shows the additivity of these two drugs. Moreover, the concentration or ratios of rilpivirine in combination with chemotherapeutic agents which provide the same inhibition effect are denoted as point $(C_{rilpivirine, 50}, C_{chemotherapeutic agents, 50})$ in the same plot. When this point is located below, on, or above the line, it shows synergy, additivity, and antagonism, respectively.

Combination Index (CI) Analysis

The combination index provides a quantitative measurement of the drug-drug interaction at the given effect level. The combination index (CI) is calculated by following equation:

$$CI = \frac{IC_{50}(A)_{pair}}{IC_{50}(A)} + \frac{IC_{50}(B)_{pair}}{IC_{50}(B)}$$

where "$IC_{50}(A)_{pair}$" refers to $IC_{50}$ of drug A when used in combination with drug B, "$IC_{50}(B)_{pair}$" refers to $IC_{50}$ of drug B when used in combination with drug A, "$IC_{50}(A)$"

refers to $IC_{50}$ of drug A when it is used alone, and "$IC_{50}(B)$" refers to $IC_{50}$ of drug B when it is used alone.

A CI of less than, equal to, and more than 1 indicates synergistic, additive, and antagonistic effect, respectively.

Xenograft Mouse Model

This study employed female BALB/c nude mice, aged 4-5 weeks, obtained from BioLasco Taiwan (under Charles River Laboratories Licensee). The animals were housed in individually ventilated cages (IVC, 36 Mini Isolator system). The allocation for 4 animals was 27×20×14 in cm. All the animals were maintained in a hygienic environment under controlled temperature (20-24° C.) and humidity (30%-70%) with 12-hour light/dark cycle. Free access to standard lab diet [MFG (Oriental Yeast Co., Ltd., Japan)] and autoclaved tap water were granted. All aspects of this work including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Pharmacology Discovery Services, Taiwan.

The IMR-32 tumor cell line was purchased from American Type Culture Collection (ATCC CCL-127, neuroblastoma) and cultured in Pharmacology Discovery Services, Taiwan. The cells were cultured in MEM medium containing 10% fetal bovine serum (FBS), 1 mM sodium pyruvate and 1 mM NEAA at 37° C. in 5% CO2 incubator. Female BALB/c nude mice were used as described in the preceding section. Viable IMR-32 cells (ATCC CCL-127) were subcutaneously (SC) implanted ($1 \times 10^7$ cells in 1:1 matrigel/complete media mixture at 0.2 mL/mouse) into the right flank of female BALB/c nude mice. Forty-one days post tumor cell implantation (group mean tumor volumes ranging 128 $mm^3$-130 $mm^3$), all the animals were randomized into sixteen study groups, each containing eight animals, and dose administrations were initiated (denoted as Day 1). All the experiments were conducted using protocols and conditions approved by the institutional animal care and use committee. The tumor volume, body weight, mortality, and signs of overt toxicity were monitored and recorded twice weekly for 28 days.

Cell Culture and Drug Treatment

The IMR-32, SK-N-SH, SH-SY5Y and SK-N-BE(2) tumor cell lines were purchased from American Type Culture Collection (ATCC, Manassas, Va.). IMR-32 and SK-N-SH were cultured in EMEM medium containing 10% fetal bovine serum (FBS), 100 U/mL penicillin and 100 U/mL streptomycin at 37° C. in 5% CO2 incubator. SH-SY5Y and SK-N-BE(2) were cultured in EMEM/F-12 containing 10% FBS, 100 U/mL penicillin and 100 U/mL streptomycin at 37° C. in 5% CO2 incubator. Cells were plated in 96 well microplates at a $3 \times 10^3$ cells density per well in culture medium. After 24 hours cells were treated with different concentrations of rilpivirine and chemotherapy agents. The cells were incubated for 72 hours and then cell proliferation was measured by 3-(4,5-dimethyl-2-thiazolyl)-2,5-diphenyl-2H-tetrazolium bromide (MTT) colorimetric assays (Sigma-Aldrich, Inc., St. Louis, Mo.). The MTT assays were performed in triplicate. Absorbance of each well was measured with a spectrophotometer (uQuant SpectroMAX Gemini Dual-scanning microplate spectro, Bio-tek Instrument Inc.) at 550 nm. Growth inhibition was expressed as the ratio of the mean absorbance of treated cells relative to that of the control.

Tumor Volume Evaluation

Tumor volume ($mm^3$) was estimated according to the prolate ellipsoid formula as:

Length×(Width)$^2$×0.5.

Tumor growth inhibition (T/C) was calculated by the following formula:

% $T/C=(T_n/C_n) \times 100\%$ $C_n$: Tumor volume measured on Day n in the control group $T_n$: Tumor volume measured on Day n in the treated group Percent tumor growth inhibition (TGI) was also calculated by the following formula:

% $TGI=(1-(T_n/C_n)) \times 100\%$

Two-way ANOVA followed by Bonferroni test was also used to ascertain the statistically significant difference in anti-tumor activity compared to the negative control group in the study (*p<0.05).

An in vivo study was performed to determine the influence of rilpivirine on rapid COJEC (cisplatin [C], vincristine [O], carboplatin [J], etoposide [E], and cyclophosphamide [C]), one of the standard regimens for the treatment of high-risk neuroblastoma patients. Rilpivirine was combined with each from rapid COJEC and assessed for the potential benefit in in the treatment of neuroblastoma in a xenograft mouse model. As will be seen in Example 4 below, rilpivirine was determined to potentiate the therapeutic effects of cisplatin, carboplatin and vincristine. By potentiating the therapeutic effect of these chemotherapeutic agents, the dosing frequency or drug concentration of the cytotoxic chemotherapy drugs during the treatment of neuroblastoma may be reduced, particularly, they may be reduced up to 75 to 90 percent of the amount of standard therapeutic protocols. Further, rilpivirine does not weaken the therapeutic effects of the chemotherapy drugs (cyclophosphamide and etoposide), showing that it can be used with the standard treatment regimen for neuroblastoma.

In Vitro Analysis

Example 1 (In Vitro Data of Rilpivirine Alone Against Multiple Neuroblastoma Cell Lines)

Figure 1B:
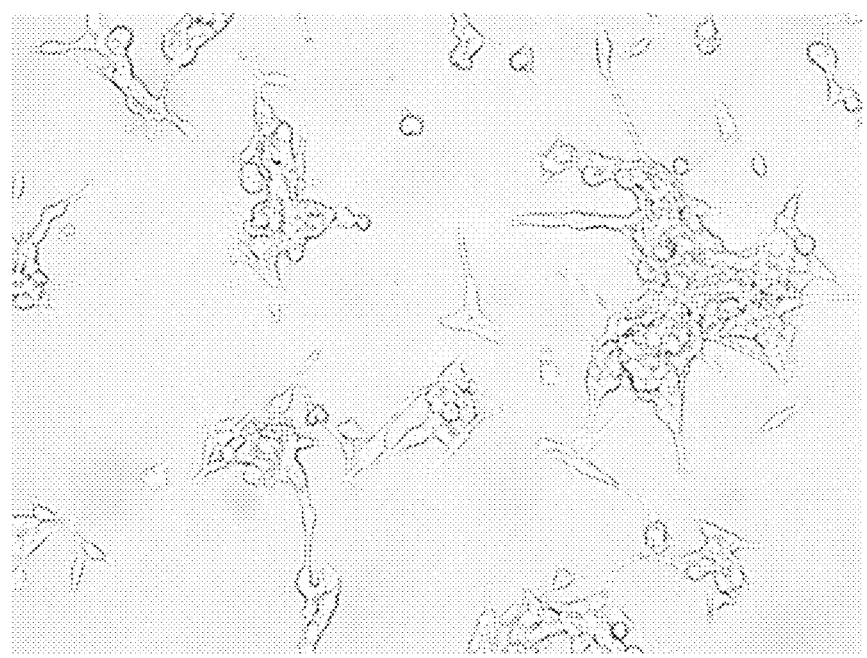
Figure 1C:
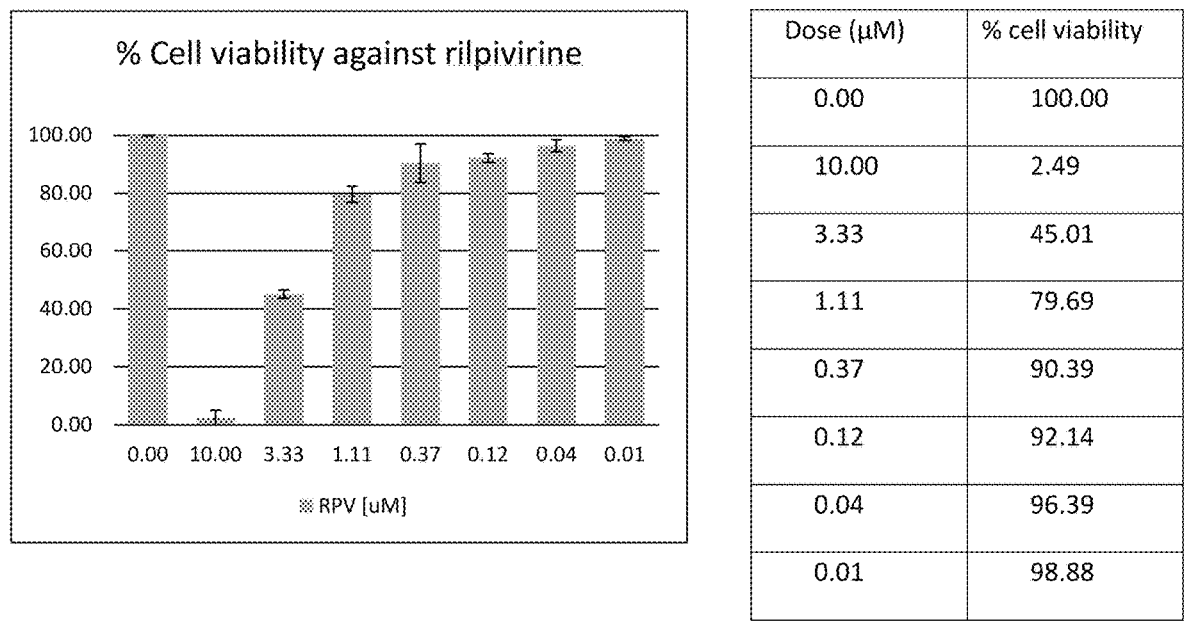

To determine the potency of rilpivirine for the inhibition of neuroblastoma cell lines, $IC_{50}$ was measured in neuroblastoma cell lines such as IMR-32, SK-N-BE(2), SK-N-SH, and SH-SY5Y (Table 1). Further, the growth of neuroblastoma cell line IMR-32 was significantly inhibited under 5 µM rilpivirine treatment for 24 hours (FIG. 1A, FIG. 1B). Percentage cell viability of IMR-32 treated with various concentrations of rilpivirine is shown in FIG. 1C.

TABLE 1

$IC_{50}$ values of rilpivirine alone in neuroblastoma cell lines

| Cell lines | IMR-32 | SK-N-BE(2) | SK-N-SH | SH-SY5Y |
|---|---|---|---|---|
| $IC_{50}$ (µM) | 2.97 | 3.37 | 2.75 | 3.12 |

Example 2 (In Vitro Data of Rilpivirine in Combination with Doxorubicin Multiple Neuroblastoma Cell Lines)

Figure 2:
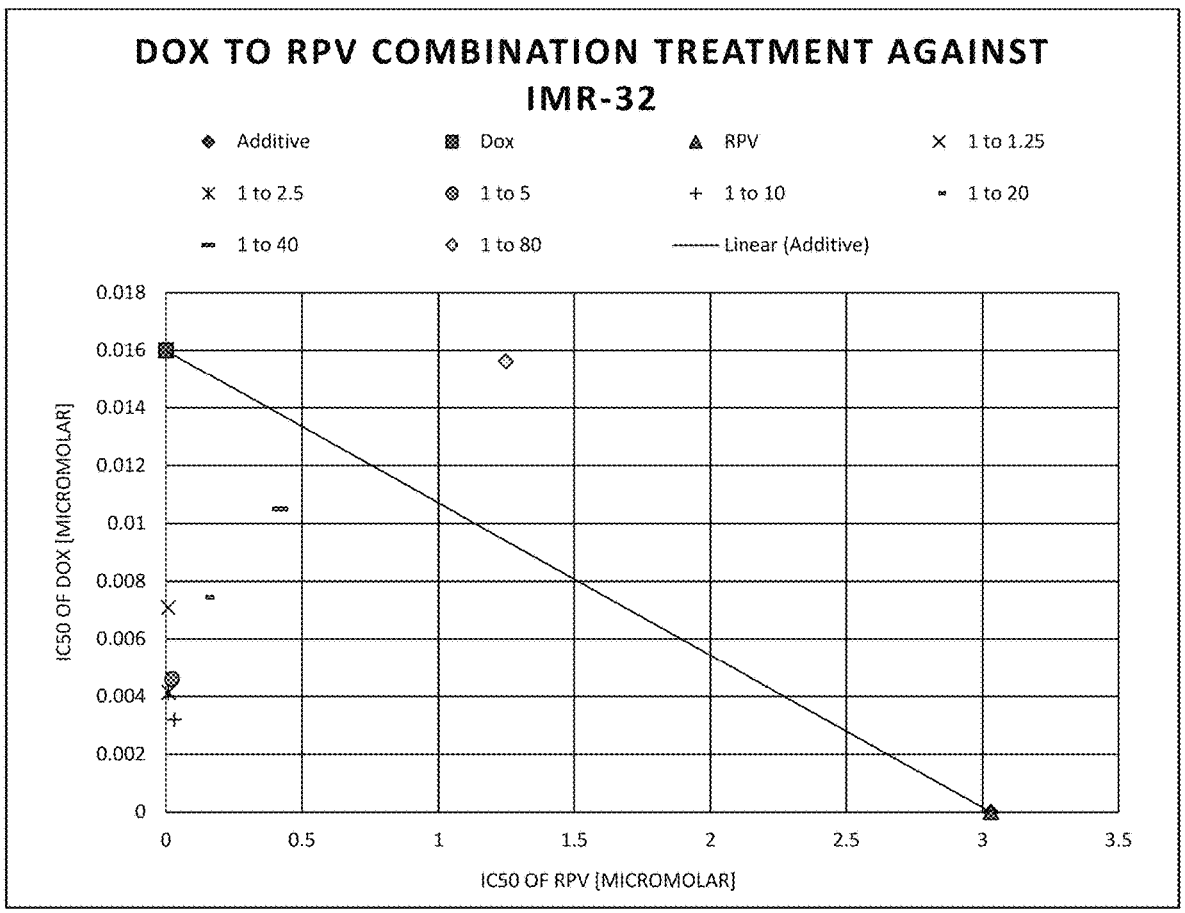
FIG. 2 presents the isobologram analysis of the combination treatment of doxorubicin (DOX) and rilpivirine (RPV) against IMR-32 cell line.
Figure 3:
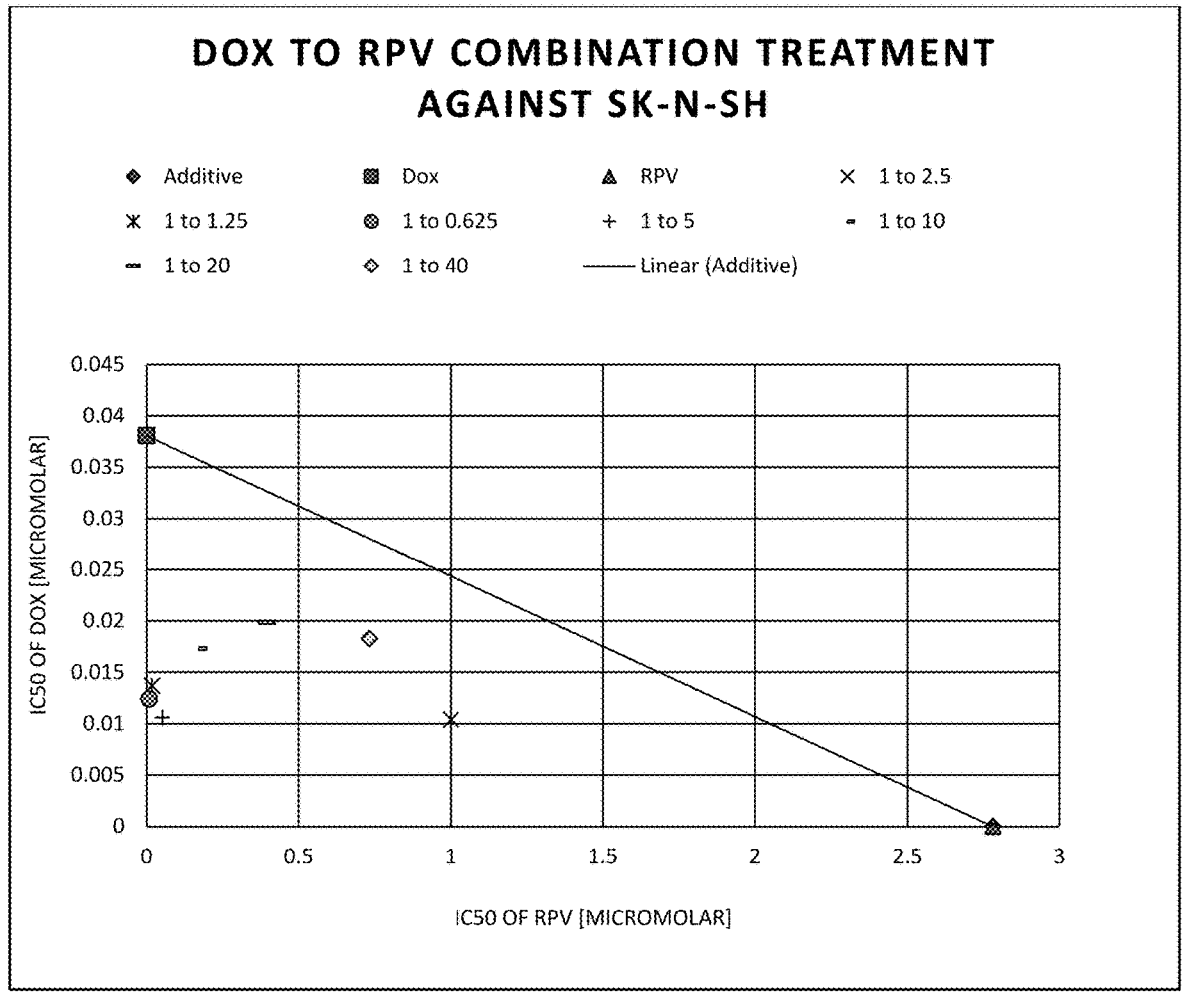
FIG. 3 presents the isobologram analysis of the combination treatment of doxorubicin (DOX) and rilpivirine (RPV) against SK-N-SH cell line.
Figure 4:
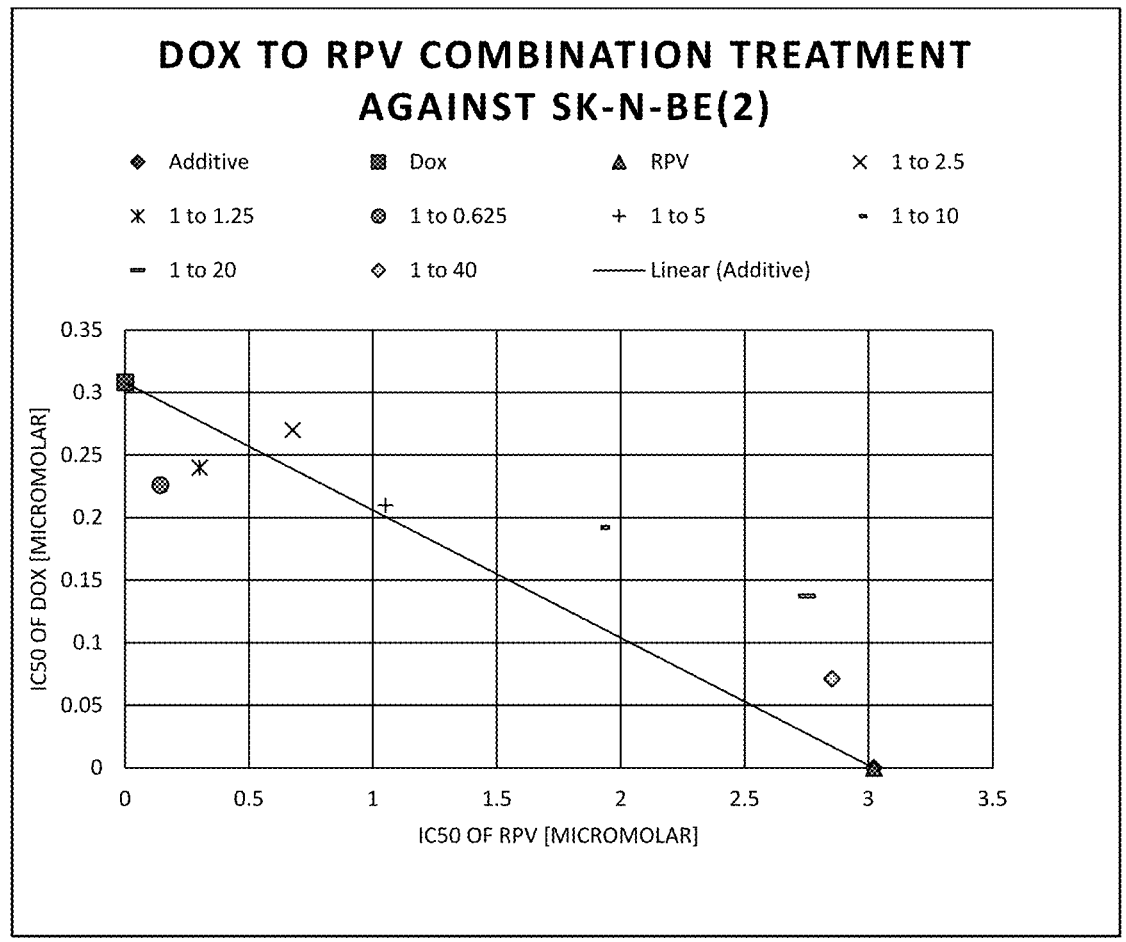
FIG. 4 presents the isobologram analysis of the combination treatment of doxorubicin (DOX) and rilpivirine (RPV) against SK-N-BE(2) cell line.
Figure 5:
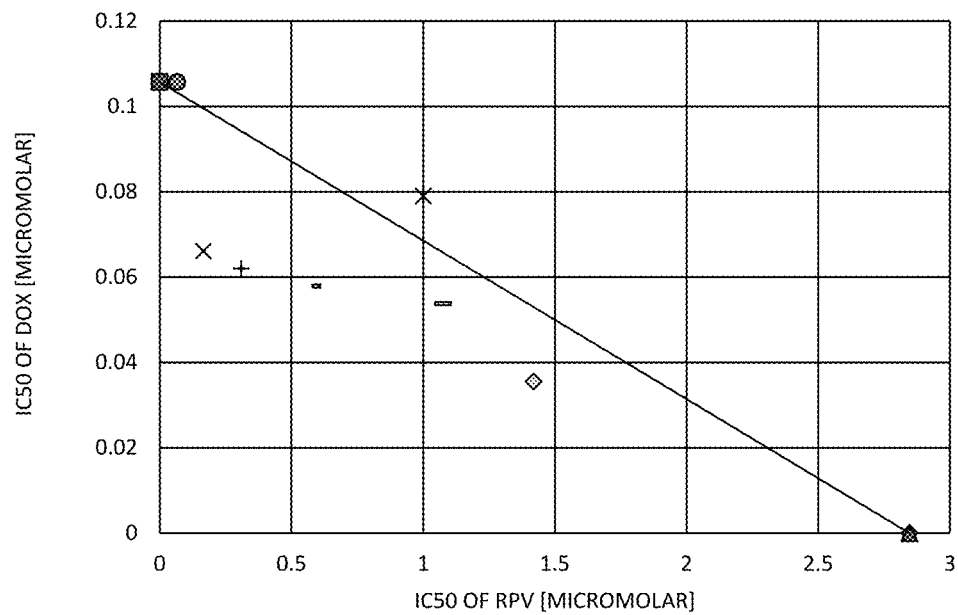
FIG. 5 presents the isobologram analysis of the combination treatment of doxorubicin (DOX) and rilpivirine (RPV) against SH-SY5Y cell line.

Doxorubicin (DOX) is a chemotherapeutic agent for cancer treatment including breast cancer, bladder cancer, Kaposi's sarcoma, lymphoma, and acute lymphocytic leukemia. Isobologram analysis shows synergistic effects with different ratios of rilpivirine and DOX against IMR-32 and SK-N-SH cell lines (FIG. 2 and FIG. 3). Combination index analysis also shows synergistic effect that CI is less than 1 (Table 2 and Table 3). As for SK-N-BE(2) and SH-SY5Y cell lines, there exists additive effects in isobologram analysis (FIG. 4 and FIG. 5) and CI is approximately close to 1 (Table 4 and Table 5).

TABLE 2

Combination index of doxorubicin (DOX) to rilpivirine (RPV) combination treatment against IMR-32 cell line Drug concentration ratio [μM (micromolar)]

| DOX | RPV | Combination index |
|---|---|---|
| 1 | 1.25 | 0.447 |
| 1 | 2.5 | 0.262 |
| 1 | 5 | 0.295 |
| 1 | 10 | 0.211 |
| 1 | 20 | 0.515 |
| 1 | 40 | 0.795 |
| 1 | 80 | 1.389 |

TABLE 3

Combination index of doxorubicin (DOX) to rilpivirine (RPV) combination treatment against SK-N-SH cell line Drug concentration ratio [μM (micromolar)]

| DOX | RPV | Combination index |
|---|---|---|
| 1 | 2.5 | 0.282 |
| 1 | 1.25 | 0.366 |
| 1 | 0.625 | 0.328 |
| 1 | 5 | 0.297 |
| 1 | 10 | 0.516 |
| 1 | 20 | 0.664 |
| 1 | 40 | 0.744 |

TABLE 4

Combination index of doxorubicin (DOX) to rilpivirine (RPV) combination treatment against SK-N-BE(2) cell line Drug concentration ratio [μM (micromolar)]

| DOX | RPV | Combination index |
|---|---|---|
| 1 | 2.5 | 1.100 |
| 1 | 1.25 | 0.879 |
| 1 | 0.625 | 0.781 |
| 1 | 5 | 1.030 |
| 1 | 10 | 1.259 |
| 1 | 20 | 1.357 |
| 1 | 40 | 1.175 |

TABLE 5

Combination index of doxorubicin (DOX) to rilpivirine (RPV) combination treatment against SH-SY5Y cell line Drug concentration ratio [μM (micromolar)]

| DOX | RPV | Combination index |
|---|---|---|
| 1 | 2.5 | 0.683 |
| 1 | 1.25 | 0.782 |
| 1 | 0.625 | 1.023 |
| 1 | 5 | 0.695 |
| 1 | 10 | 0.751 |
| 1 | 20 | 0.887 |
| 1 | 40 | 0.835 |

Example 3 (In Vitro Data of Rilpivirine in Combination with Perfosfamide Against Multiple Neuroblastoma Cell Lines)

Figure 6:
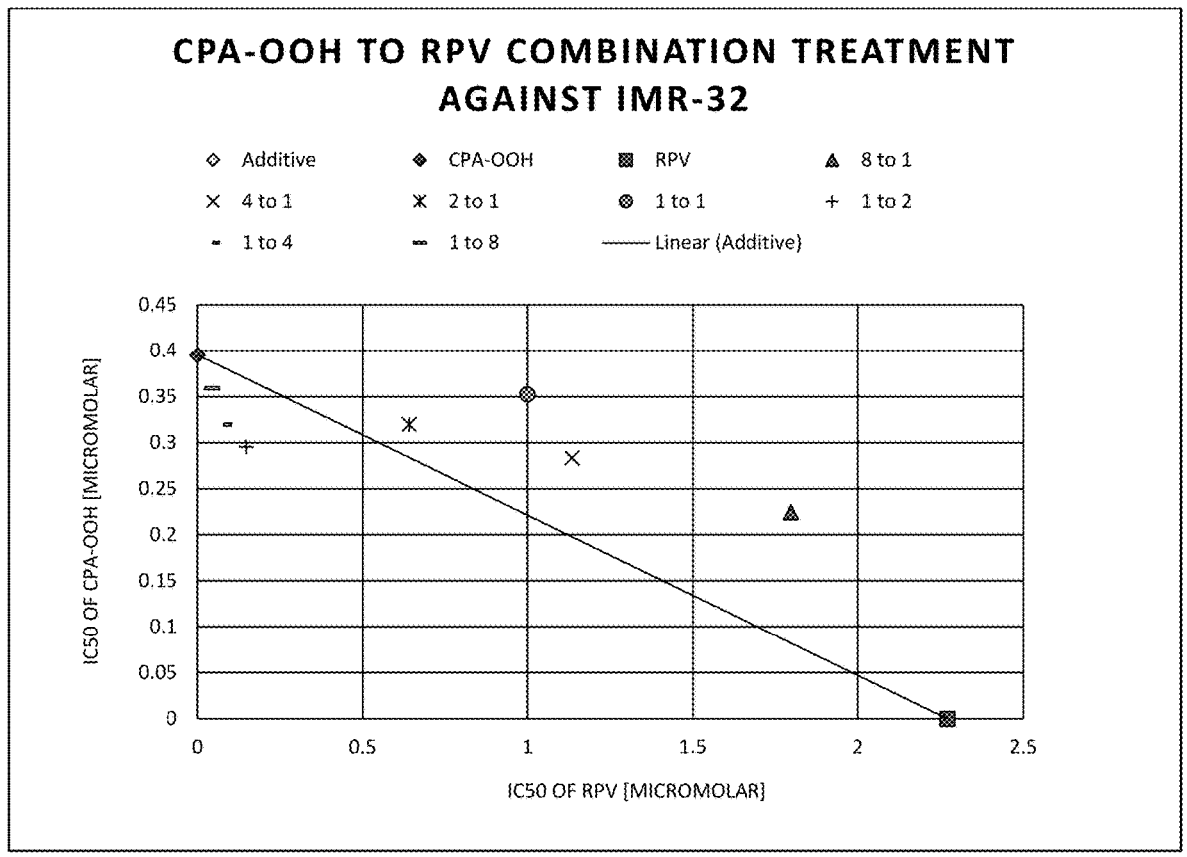
FIG. 6 presents the isobologram analysis of the combination treatment of 4-hydroperoxycyclophosphamide (CPA-OOH) and rilpivirine (RPV) against IMR-32 cell line.
Figure 7:
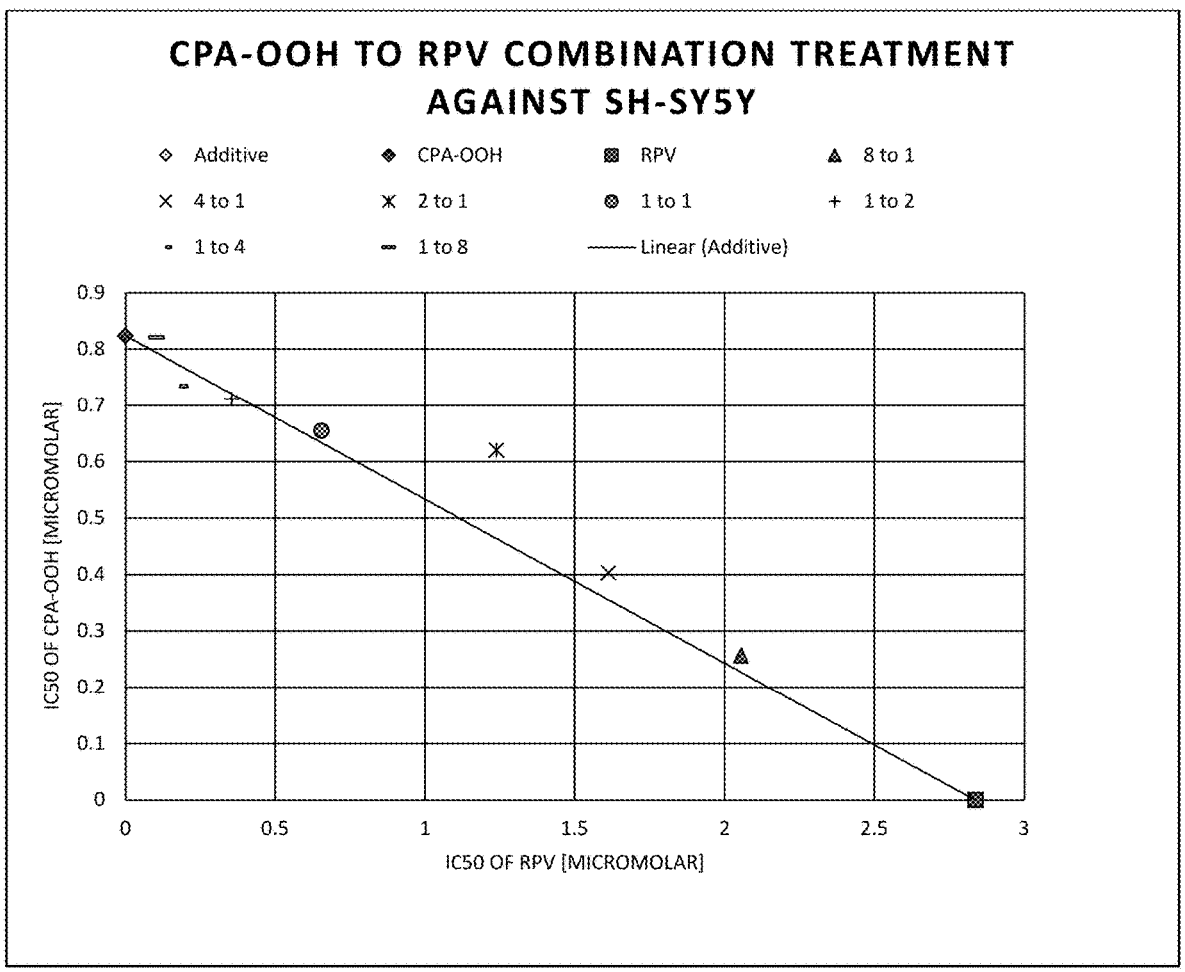
FIG. 7 presents the isobologram analysis of the combination treatment of 4-hydroperoxycyclophosphamide (CPA-OOH) and rilpivirine (RPV) against SH-SY5Y cell line.
Figure 8:
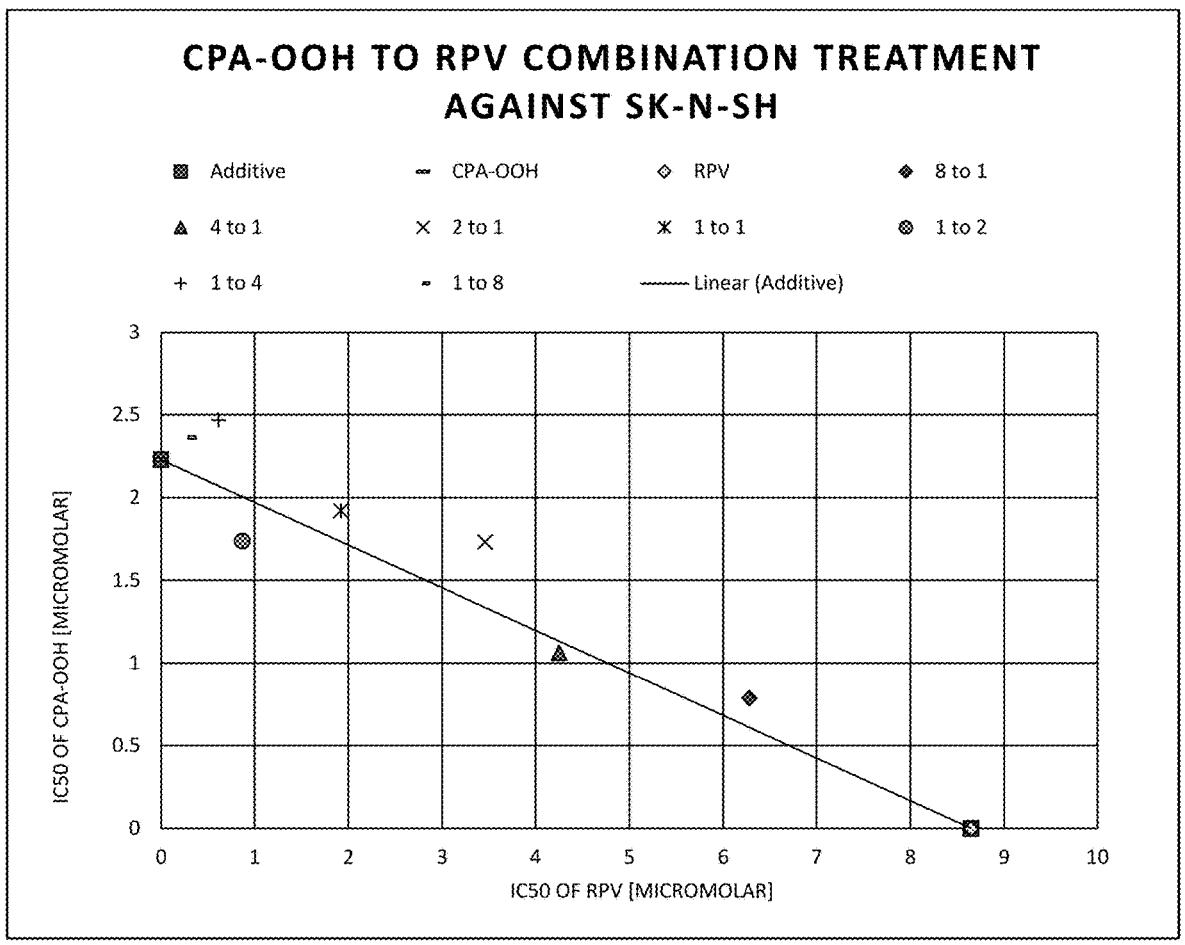
FIG. 8 presents the isobologram analysis of the combination treatment of 4-hydroperoxycyclophosphamide (CPA-OOH) and rilpivirine (RPV) against SK-N-SH cell line.
Figure 9:
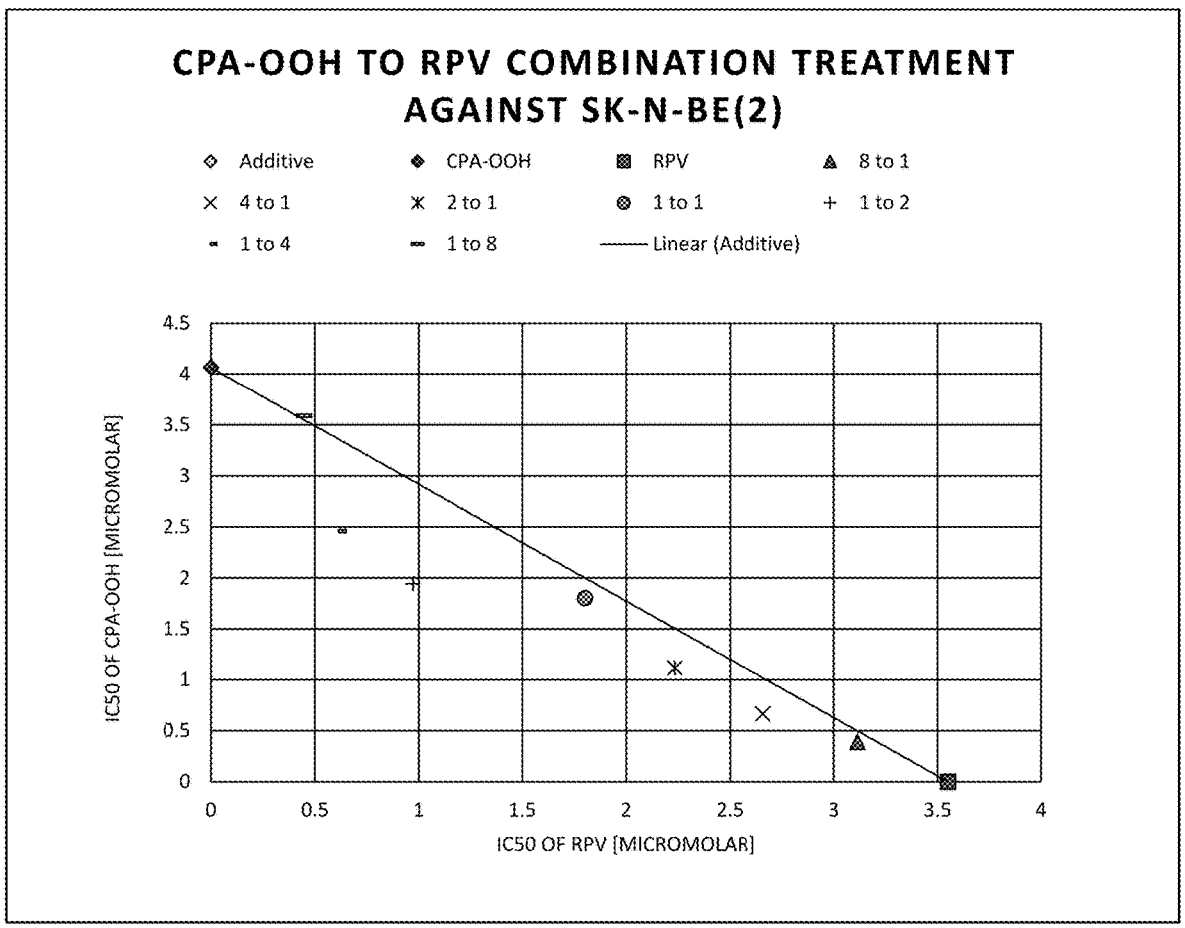
FIG. 9 presents the isobologram analysis of the combination treatment of 4-hydroperoxycyclophosphamide (CPA-OOH) and rilpivirine (RPV) against SK-N-BE(2) cell line.

4-hydroperoxycyclophosphamide (or perfosfamide), a cyclophosphamide analog, was an experimental drug for blood cancer treatment such as acute myeloid leukemia. The isobologram analysis shows additive and mild antagonistic effects with different ratios of 4-hydroperoxycyclophosphamide and rilpivirine against IMR-32 (FIG. 6), SH-SY5Y (FIG. 7), SK-N-SH (FIG. 8) and SK-N-BE(2) cell lines (FIG. 9). The combination index analysis also shows additive that CI is between 0.9 to 1.1 and antagonistic effect that CI is more than 1.1 (Table 6 to Table 9).

TABLE 6

Combination index of 4-hydroperoxycyclophosphamide (CPA-OOH) to rilpivirine (RPV) combination treatment against IMR-32 cell line Drug concentration ratio [μM (micromolar)]

| CPA-OOH | RPV | Combination index |
|---|---|---|
| 1 | 8 | 1.360 |
| 1 | 4 | 1.217 |
| 1 | 2 | 1.091 |
| 1 | 1 | 1.047 |
| 2 | 1 | 0.813 |
| 4 | 1 | 0.844 |
| 8 | 1 | 0.929 |

TABLE 7

Combination index of 4-hydroperoxycyclophosphamide (CPA-OOH) to rilpivirine (RPV) combination treatment against SH-SY5Y cell line Drug concentration ratio [μM (micromolar)]

| CPA-OOH | RPV | Combination index |
|---|---|---|
| 1 | 8 | 1.036 |
| 1 | 4 | 1.057 |
| 1 | 2 | 1.190 |
| 1 | 1 | 1.026 |
| 2 | 1 | 0.989 |
| 4 | 1 | 0.956 |
| 8 | 1 | 1.033 |

TABLE 8

Combination index of 4-hydroperoxycyclophosphamide (CPA-OOH) to rilpivirine (RPV) combination treatment against SK-N-SH cell line

| Drug concentration ratio [μM (micromolar)] | | Combination index |
|---|---|---|
| CPA-OOH | RPV | |
| 1 | 8 | 1.079 |
| 1 | 4 | 0.969 |
| 1 | 2 | 1.178 |
| 1 | 1 | 1.083 |
| 2 | 1 | 0.880 |
| 4 | 1 | 1.178 |
| 8 | 1 | 1.094 |

TABLE 9

Combination index of 4-hydroperoxycyclophosphamide (CPA-OOH) to rilpivirine (RPV) combination treatment against SK-N-BE(2) cell line

| Drug concentration ratio [μM (micromolar)] | | Combination index |
|---|---|---|
| CPA-OOH | RPV | |
| 1 | 8 | 0.973 |
| 1 | 4 | 0.913 |
| 1 | 2 | 0.904 |
| 1 | 1 | 0.951 |
| 2 | 1 | 0.752 |
| 4 | 1 | 0.778 |
| 8 | 1 | 1.010 |

Example 4 (In Vitro Data of Rilpivirine in Combination with Cisplatin Against Multiple Neuroblastoma Cell Lines)

Figure 10:
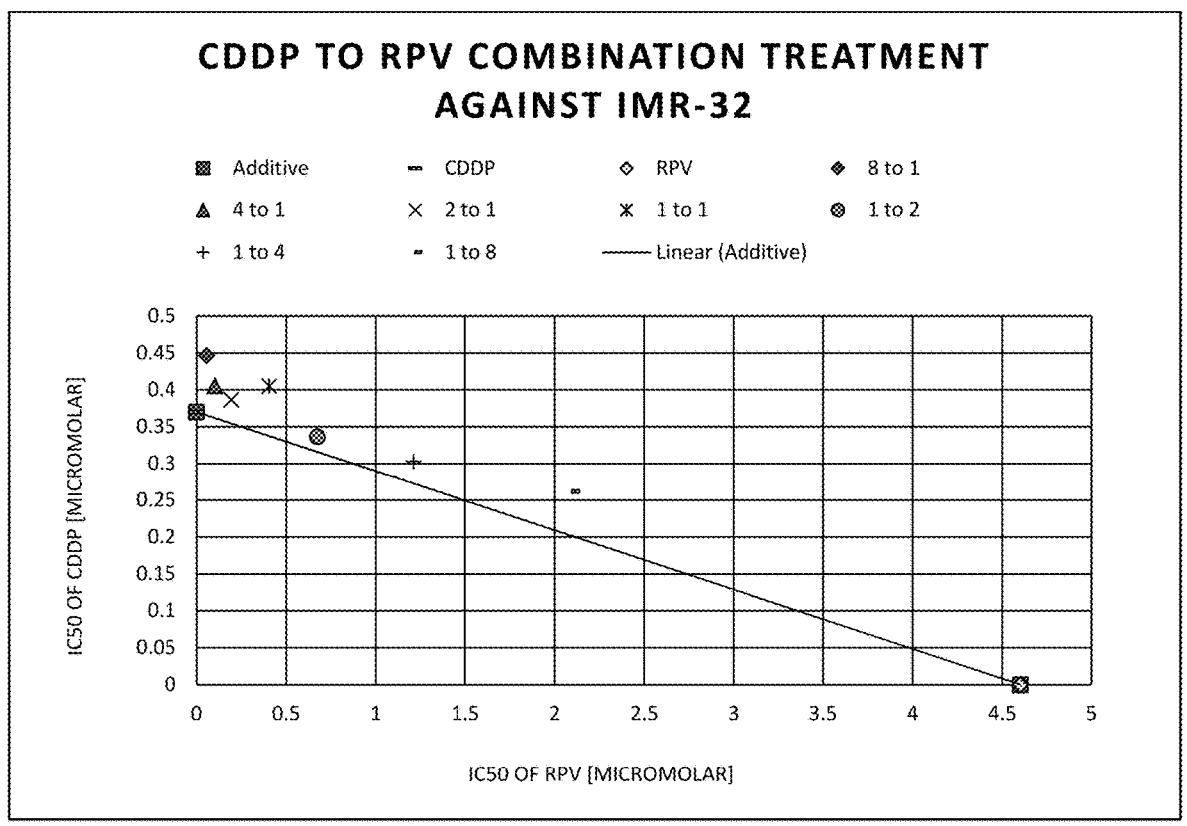
FIG. 10 presents the isobologram analysis of the combination treatment cisplatin (CDDP) and of rilpivirine (RPV) against IMR-32 cell line.
Figure 11:
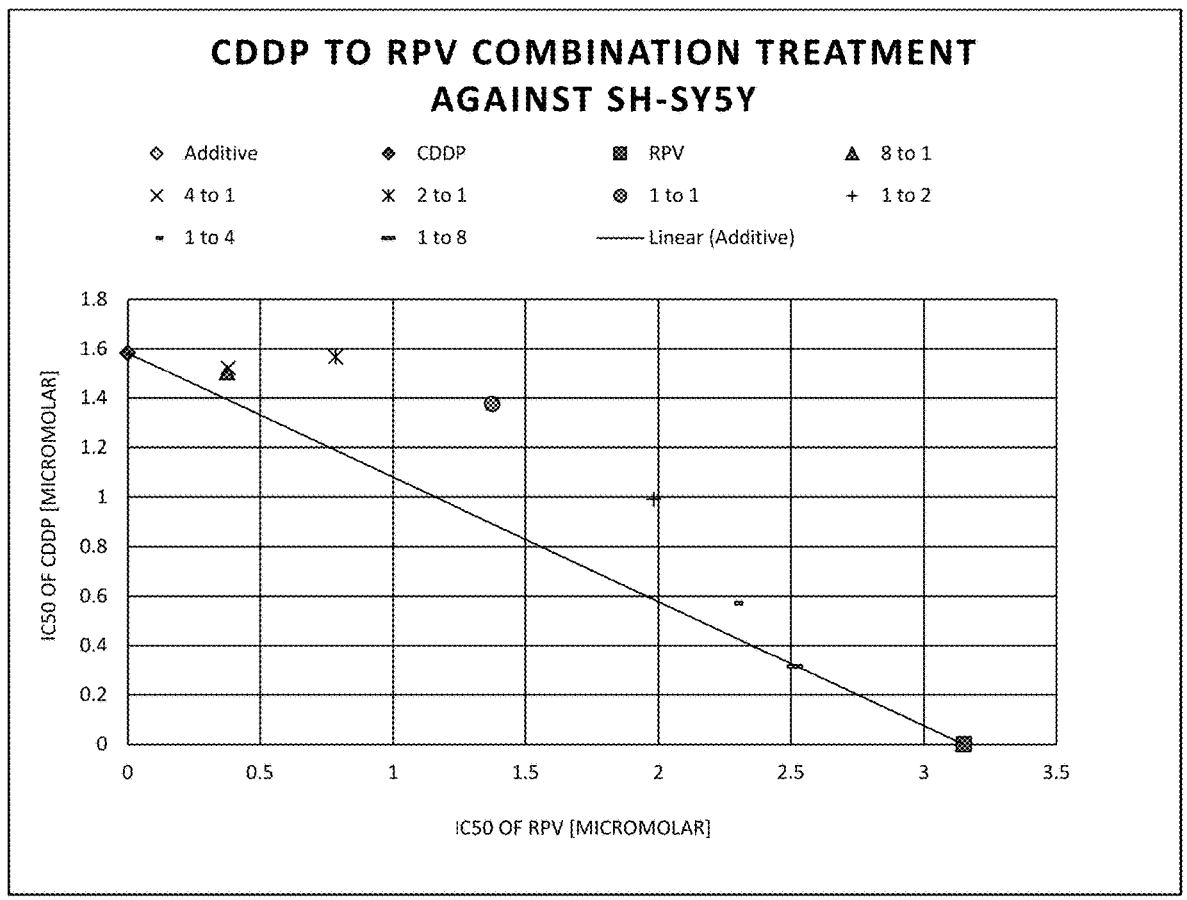
FIG. 11 presents the isobologram analysis of the combination treatment cisplatin (CDDP) and of rilpivirine (RPV) against SH-SY5Y cell line.
Figure 12:
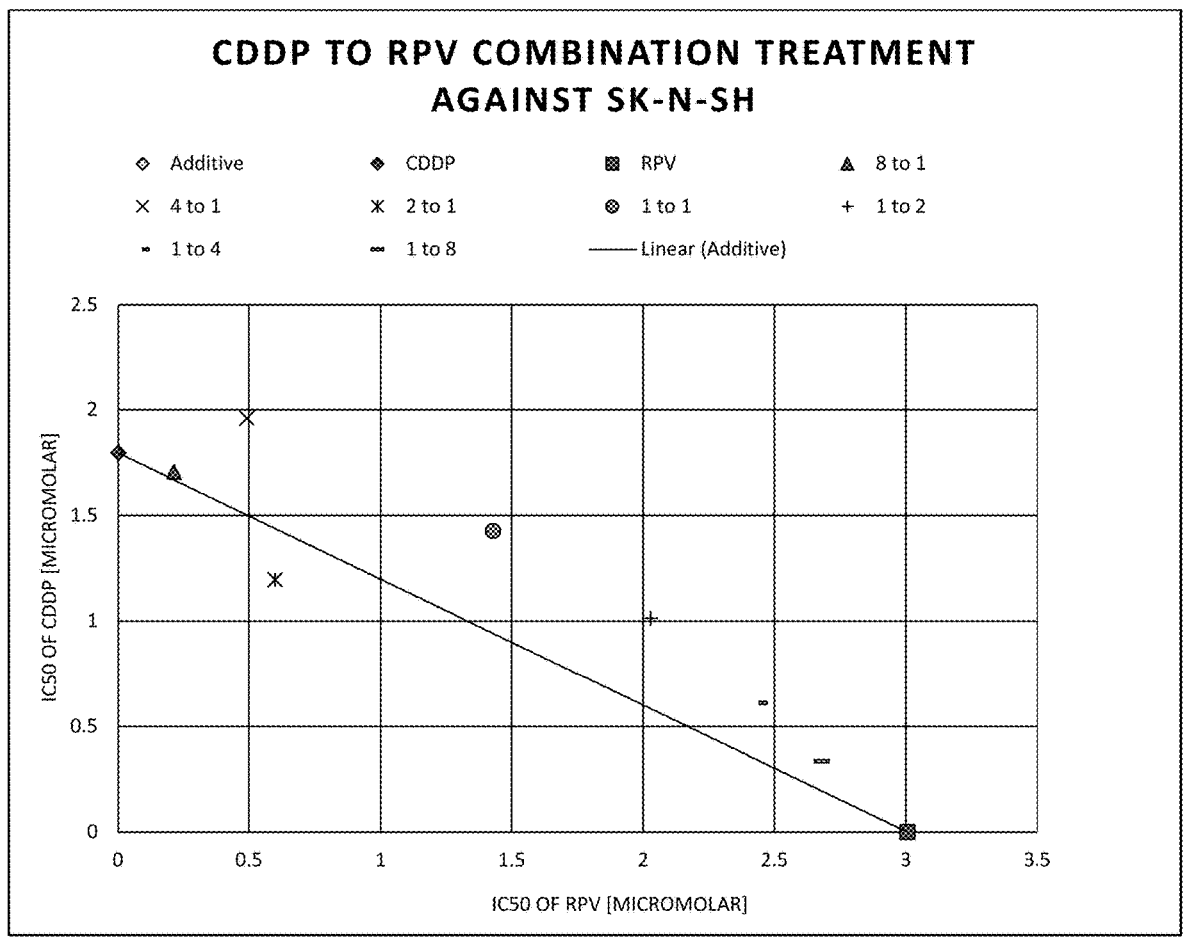
FIG. 12 presents the isobologram analysis of the combination treatment cisplatin (CDDP) and of rilpivirine (RPV) against SK-N-SH cell line.
Figure 13:
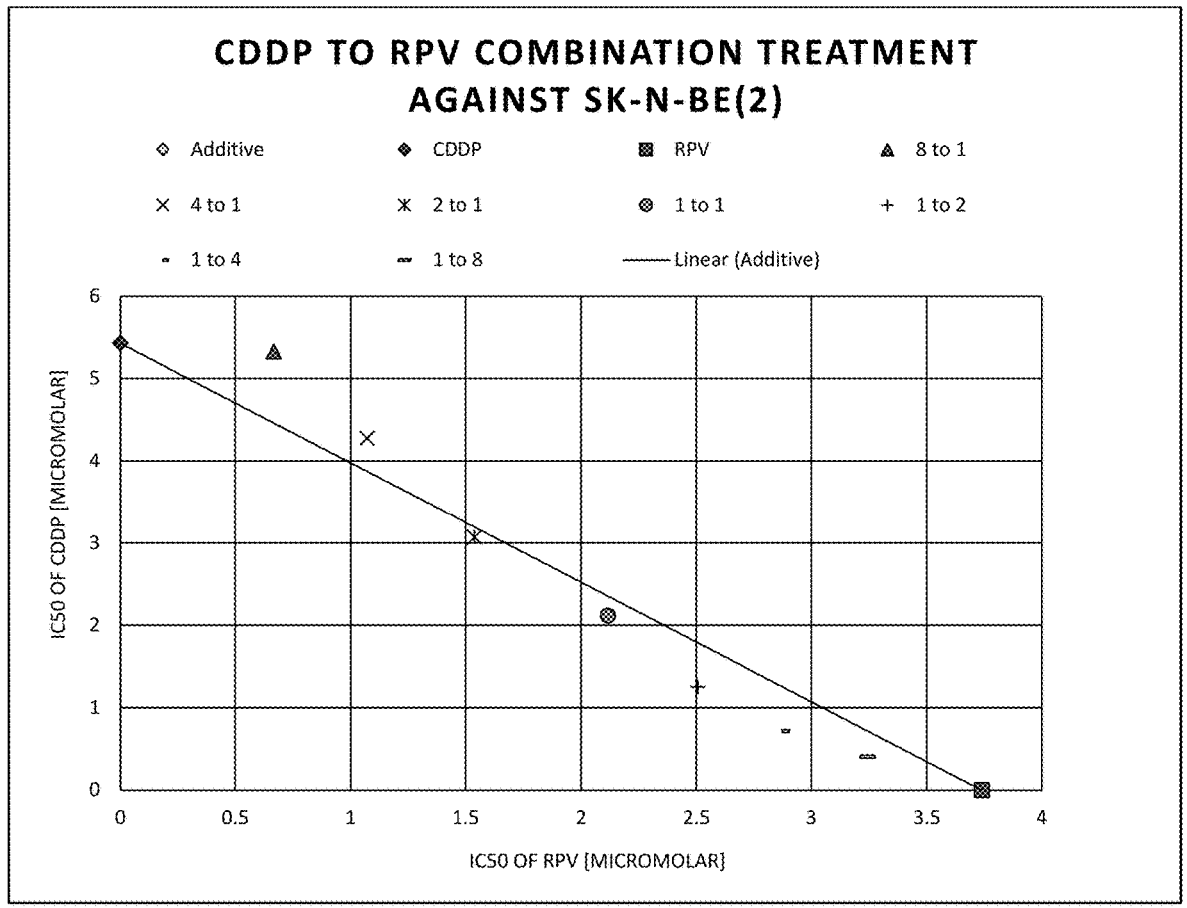
FIG. 13 presents the isobologram analysis of the combination treatment cisplatin (CDDP) and of rilpivirine (RPV) against SK-N-BE(2) cell line.

Cisplatin (CDDP) is a chemotherapeutic agent for cancer treatment including testicular cancer, ovarian cancer, cervical cancer, breast cancer, bladder cancer, head and neck cancer, esophageal cancer, lung cancer, mesothelioma, brain tumors and neuroblastoma. Isobologram analysis shows additive and mild antagonistic effects with different ratios of rilpivirine and CDDP against IMR-32 (FIG. 10), SH-SY5Y (FIG. 11), SK-N-SH (FIG. 12), and SK-N-BE(2) cell lines (FIG. 13). The combination index analysis also shows additive effect that CI is between 0.9 and 1.1 and antagonistic effect that CI is more than 1.1 (Table 10 to Table 13).

TABLE 10

Combination index of cisplatin (CDDP) to rilpivirine (RPV) combination treatment against IMR-32 cell line

| Drug concentration ratio [μM (micromolar)] | | Combination Index |
|---|---|---|
| CDDP | RPV | |
| 8 | 1 | 1.219 |
| 4 | 1 | 1.117 |
| 2 | 1 | 1.086 |
| 1 | 1 | 1.183 |
| 1 | 2 | 1.056 |
| 1 | 4 | 1.081 |
| 1 | 8 | 1.164 |

TABLE 11

Combination index of cisplatin (CDDP) to rilpivirine (RPV) combination treatment against SH-SY5Y cell line

| Drug concentration ratio [μM (micromolar)] | | Combination Index |
|---|---|---|
| CDDP | RPV | |
| 8 | 1 | 1.069 |
| 4 | 1 | 1.082 |
| 2 | 1 | 1.239 |
| 1 | 1 | 1.305 |
| 1 | 2 | 1.255 |
| 1 | 4 | 1.088 |
| 1 | 8 | 0.997 |

TABLE 12

Combination index of cisplatin (CDDP) to rilpivirine (RPV) combination treatment against SK-N-SH cell line

| Drug concentration ratio [μM (micromolar)] | | Combination Index |
|---|---|---|
| CDDP | RPV | |
| 8 | 1 | 1.021 |
| 4 | 1 | 1.255 |
| 2 | 1 | 0.865 |
| 1 | 1 | 1.270 |
| 1 | 2 | 1.239 |
| 1 | 4 | 1.153 |
| 1 | 8 | 1.078 |

TABLE 13

Combination index of cisplatin (CDDP) to rilpivirine (RPV) combination treatment against SK-N-BE(2) cell line

| Drug concentration ratio [μM (micromolar)] | | Combination Index |
|---|---|---|
| CDDP | RPV | |
| 8 | 1 | 1.159 |
| 4 | 1 | 1.074 |
| 2 | 1 | 0.977 |
| 1 | 1 | 0.955 |
| 1 | 2 | 0.901 |
| 1 | 4 | 0.901 |
| 1 | 8 | 0.942 |

Example 5 (In Vitro Data of Rilpivirine in Combination with Etoposide Against Multiple Neuroblastoma Cell Lines)

Figure 14:
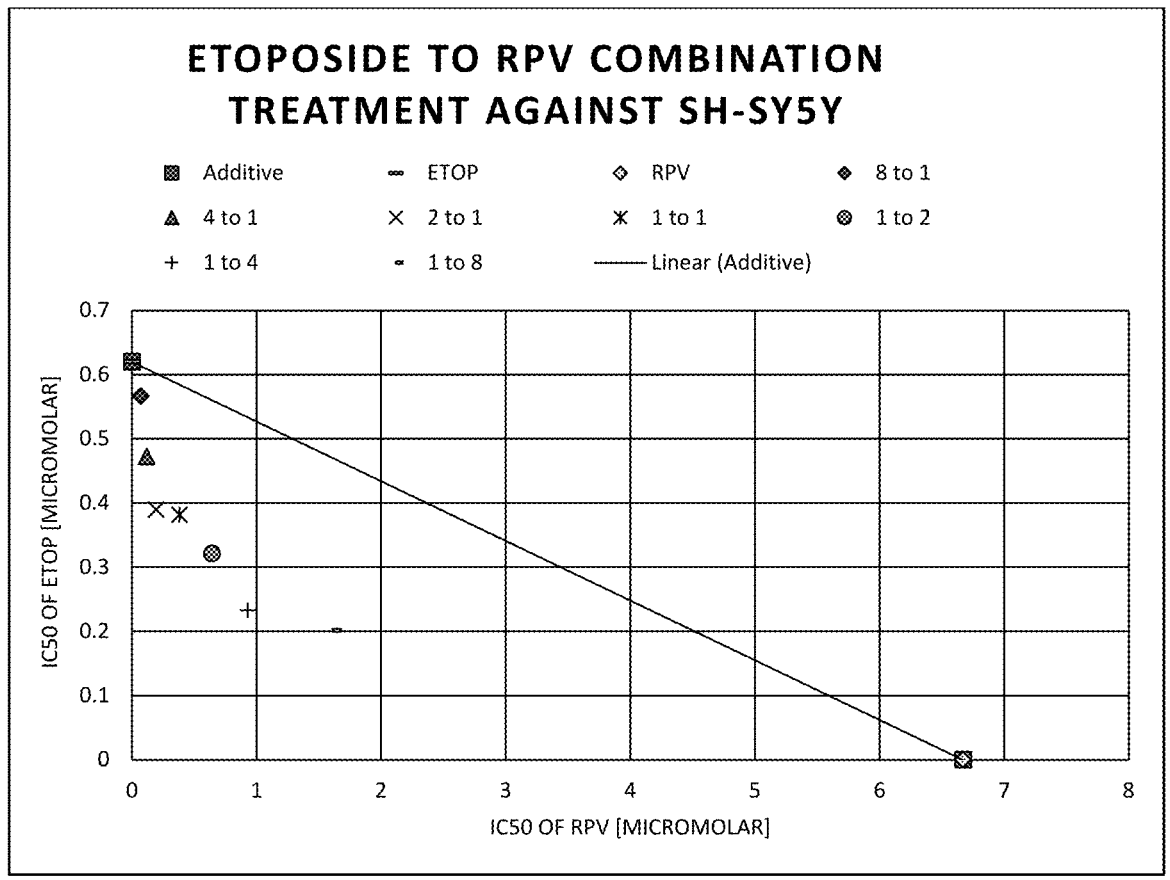
FIG. 14 presents the isobologram analysis of the combination treatment etoposide (ETOP) and of rilpivirine (RPV) against SH-SY5Y cell line.
Figure 15:
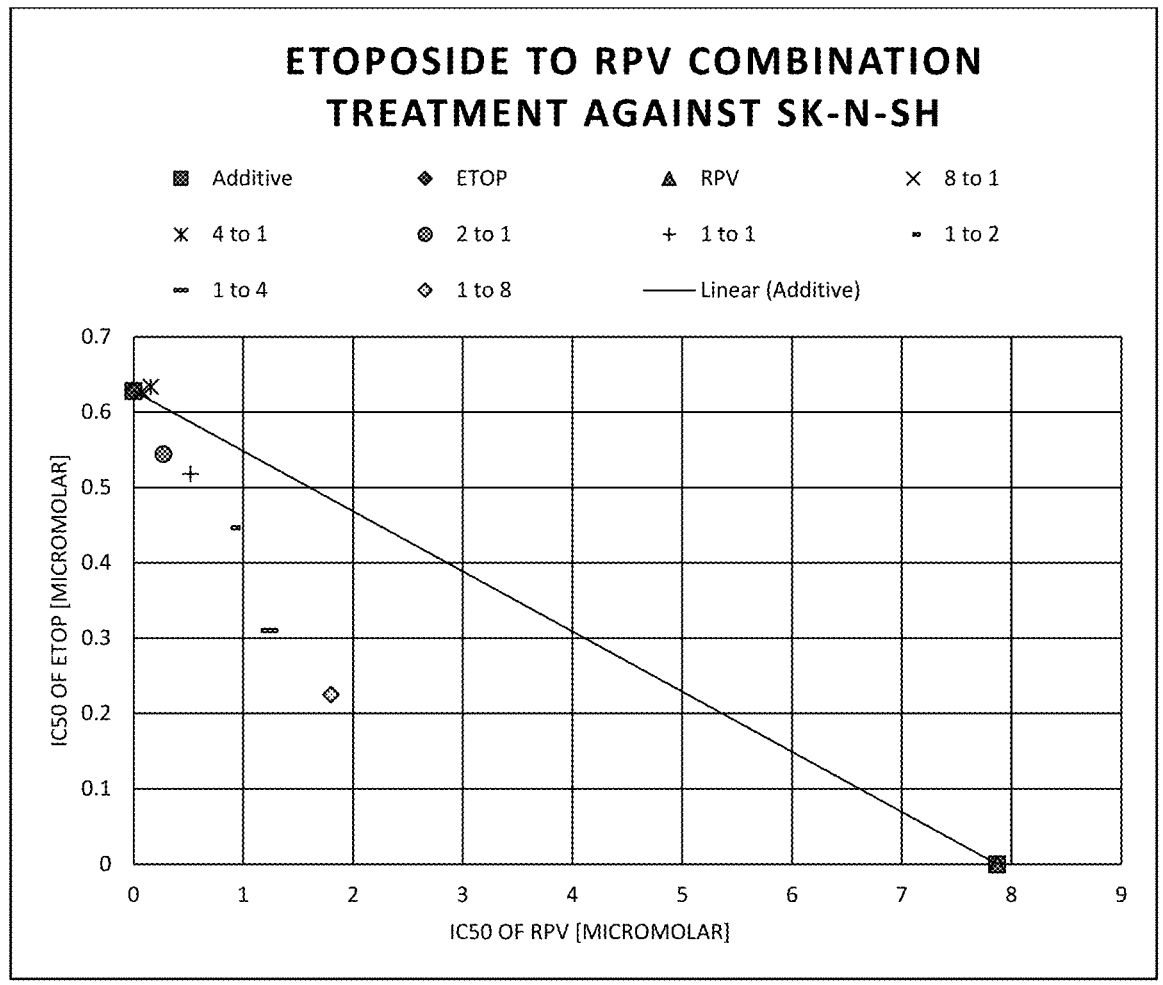
FIG. 15 presents the isobologram analysis of the combination treatment etoposide (ETOP) and of rilpivirine (RPV) against SK-N-SH cell line.
Figure 16:
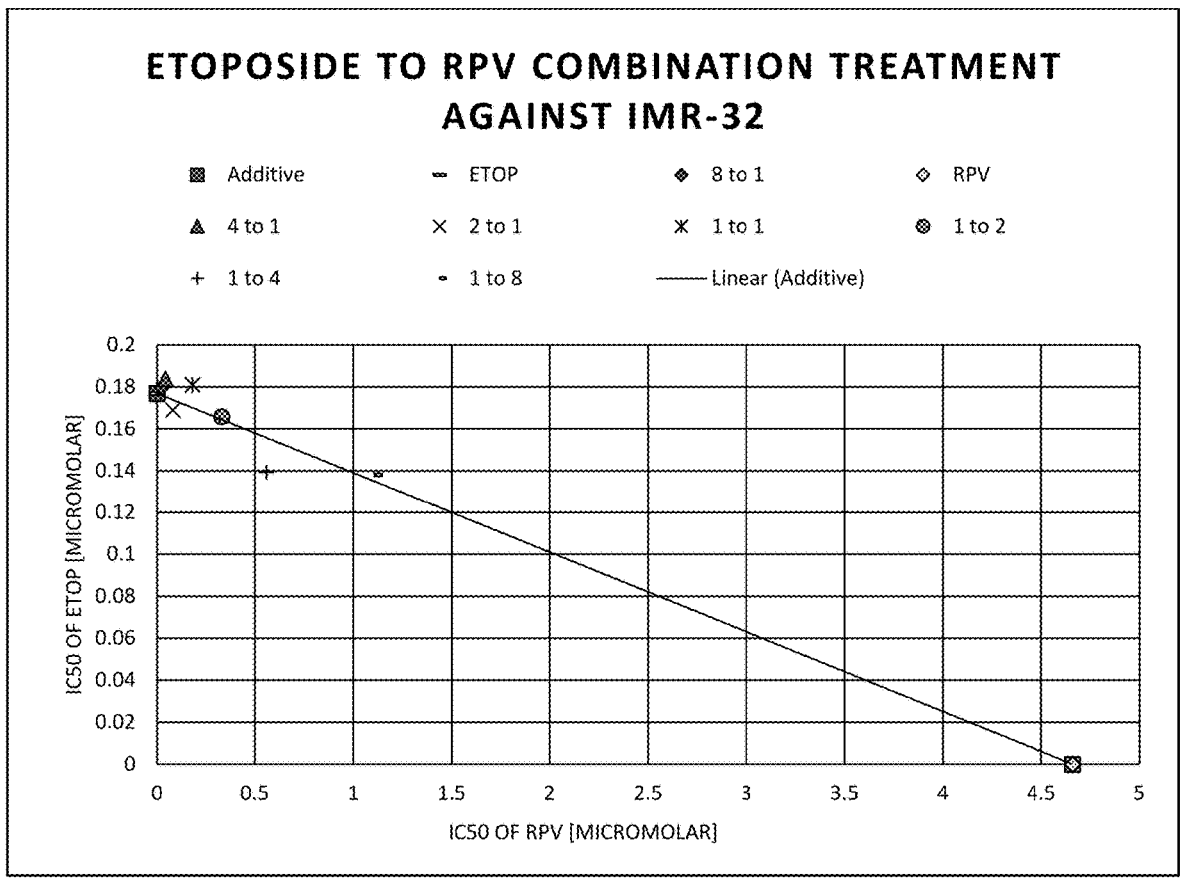
FIG. 16 presents the isobologram analysis of the combination treatment etoposide (ETOP) and of rilpivirine (RPV) against IMR-32 cell line.
Figure 17:
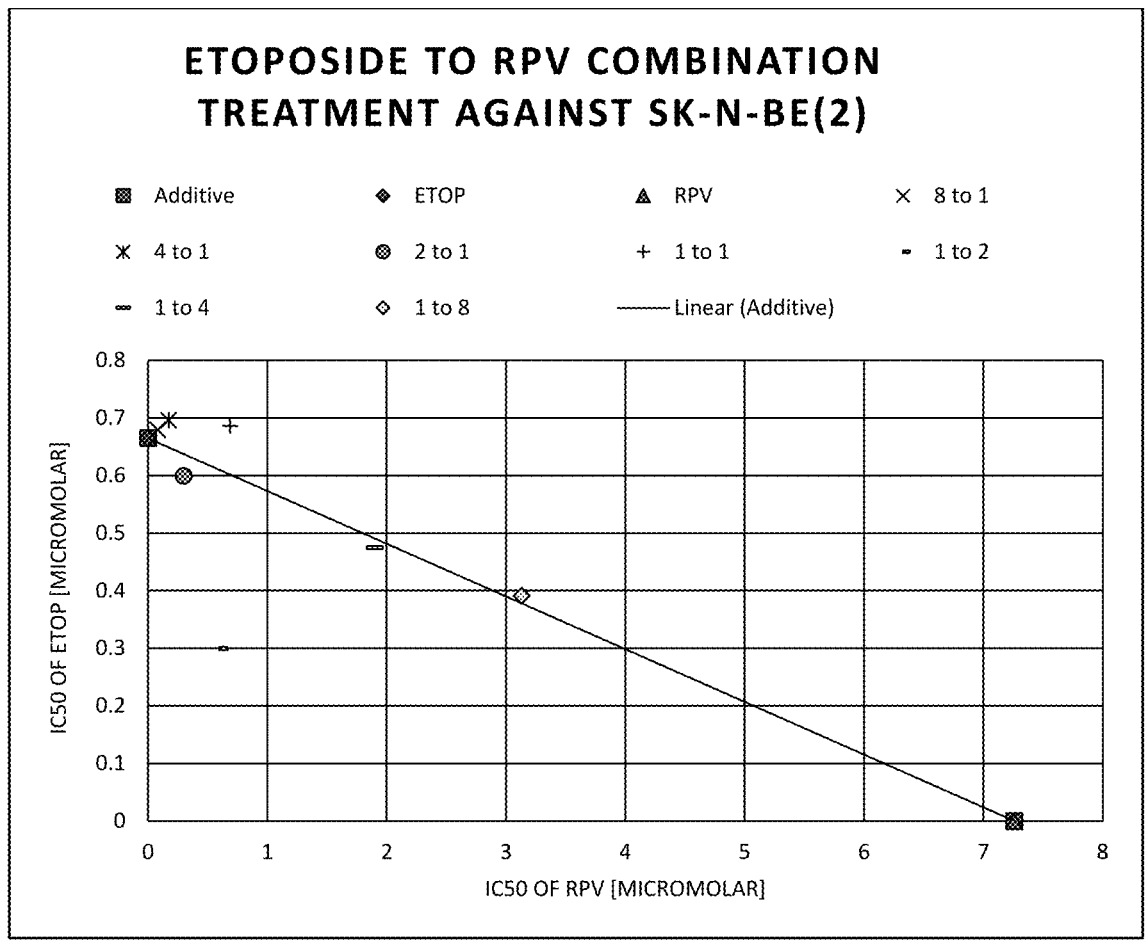
FIG. 17 presents the isobologram analysis of the combination treatment etoposide (ETOP) and of rilpivirine (RPV) against SK-N-BE(2) cell line.

Etoposide (ETOP) is a chemotherapy medication used for cancer treatment including testicular cancer, lung cancer, lymphoma, leukemia, neuroblastoma, and ovarian cancer. Isobologram analysis shows synergistic effects with different ratios of rilpivirine and ETOP against SH-SY5Y and SK-N-SH cell lines (FIG. 14 and FIG. 15) and the combination index analysis also shows synergistic effect that the CI is less than 1 (Table 14 and Table 15). As for IMR-32 cell line and SK-N-BE(2) cell line, there exists additive effects in isobologram analysis (FIG. 16 and FIG. 17) and CI is approximately close to 1 (Table 16 and Table 17).

TABLE 14

Combination index of etoposide (ETOP) to rilpivirine (RPV) combination treatment against SH-SY5Y cell line

| Drug concentration ratio [μM (micromolar)] | | Combination Index |
|---|---|---|
| ETOP | RPV | |
| 8 | 1 | 0.925 |
| 4 | 1 | 0.779 |
| 2 | 1 | 0.657 |
| 1 | 1 | 0.673 |
| 1 | 2 | 0.615 |
| 1 | 4 | 0.515 |
| 1 | 8 | 0.567 |

TABLE 15

Combination index of etoposide (ETOP) to rilpivirine (RPV) combination treatment against SK-N-SH cell line

| Drug concentration ratio [μM (micromolar)] | | Combination Index |
|---|---|---|
| ETOP | RPV | |
| 8 | 1 | 1.009 |
| 4 | 1 | 1.028 |
| 2 | 1 | 0.901 |
| 1 | 1 | 0.891 |
| 1 | 2 | 0.824 |
| 1 | 4 | 0.651 |
| 1 | 8 | 0.587 |

TABLE 16

Combination index of etoposide (ETOP) to rilpivirine (RPV) combination treatment against IMR-32 cell line

| Drug concentration ratio [μM (micromolar)] | | Combination Index |
|---|---|---|
| ETOP | RPV | |
| 8 | 1 | 1.020 |
| 4 | 1 | 1.048 |
| 2 | 1 | 0.972 |
| 1 | 1 | 1.061 |
| 1 | 2 | 1.008 |
| 1 | 4 | 0.907 |
| 1 | 8 | 1.018 |

TABLE 17

Combination index of etoposide (ETOP) to rilpivirine (RPV) combination treatment against SK-N-BE(2) cell line

| Drug concentration ratio [μM (micromolar)] | | Combination Index |
|---|---|---|
| ETOP | RPV | |
| 8 | 1 | 1.033 |
| 4 | 1 | 1.071 |
| 2 | 1 | 0.942 |
| 1 | 1 | 1.126 |
| 1 | 2 | 0.533 |
| 1 | 4 | 0.976 |
| 1 | 8 | 1.020 |

Example 6 (In Vitro Data of Rilpivirine in Combination with Vincristine Multiple Neuroblastoma Cell Lines)

Figure 18:
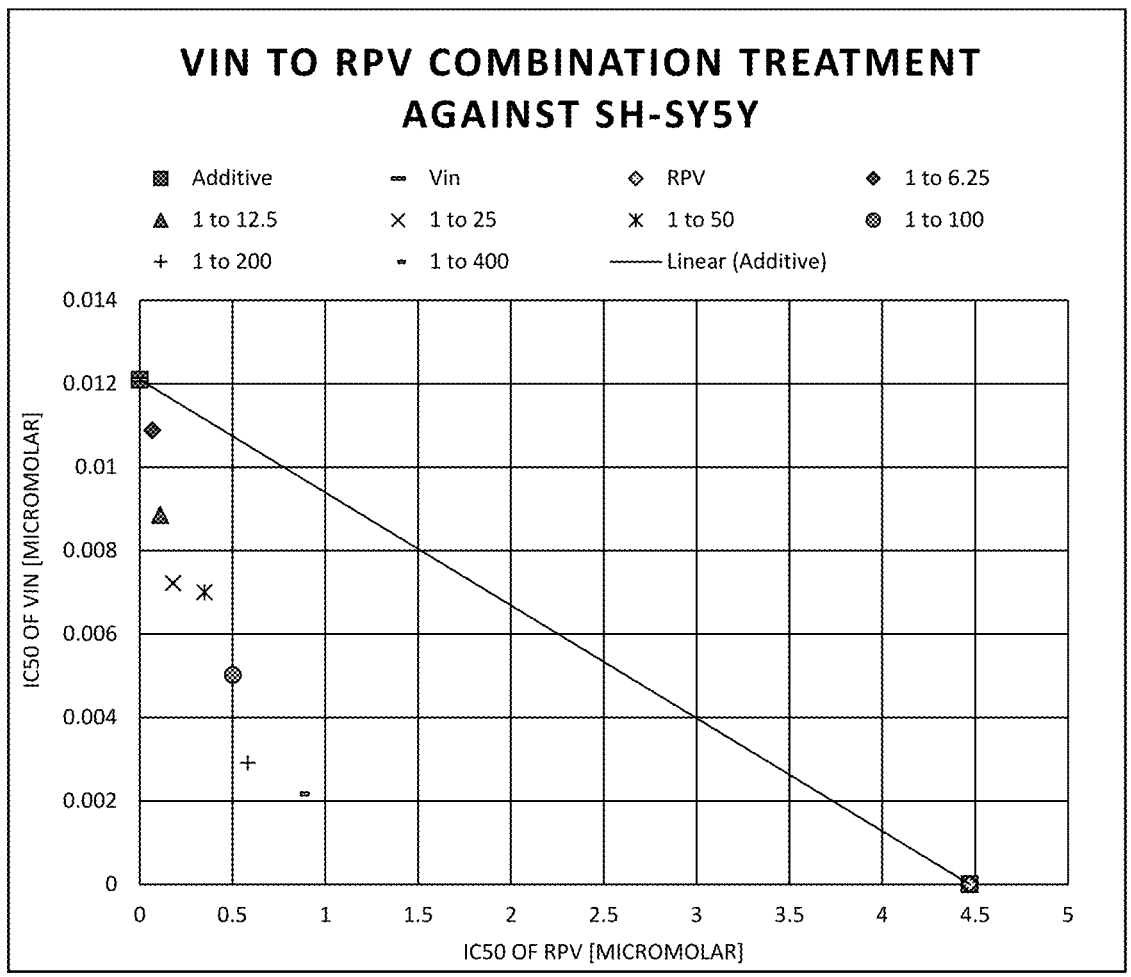
FIG. 18 presents the isobologram analysis of the combination treatment vincristine (Vin) and of rilpivirine (RPV) against SH-SY5Y cell line.
Figure 19:
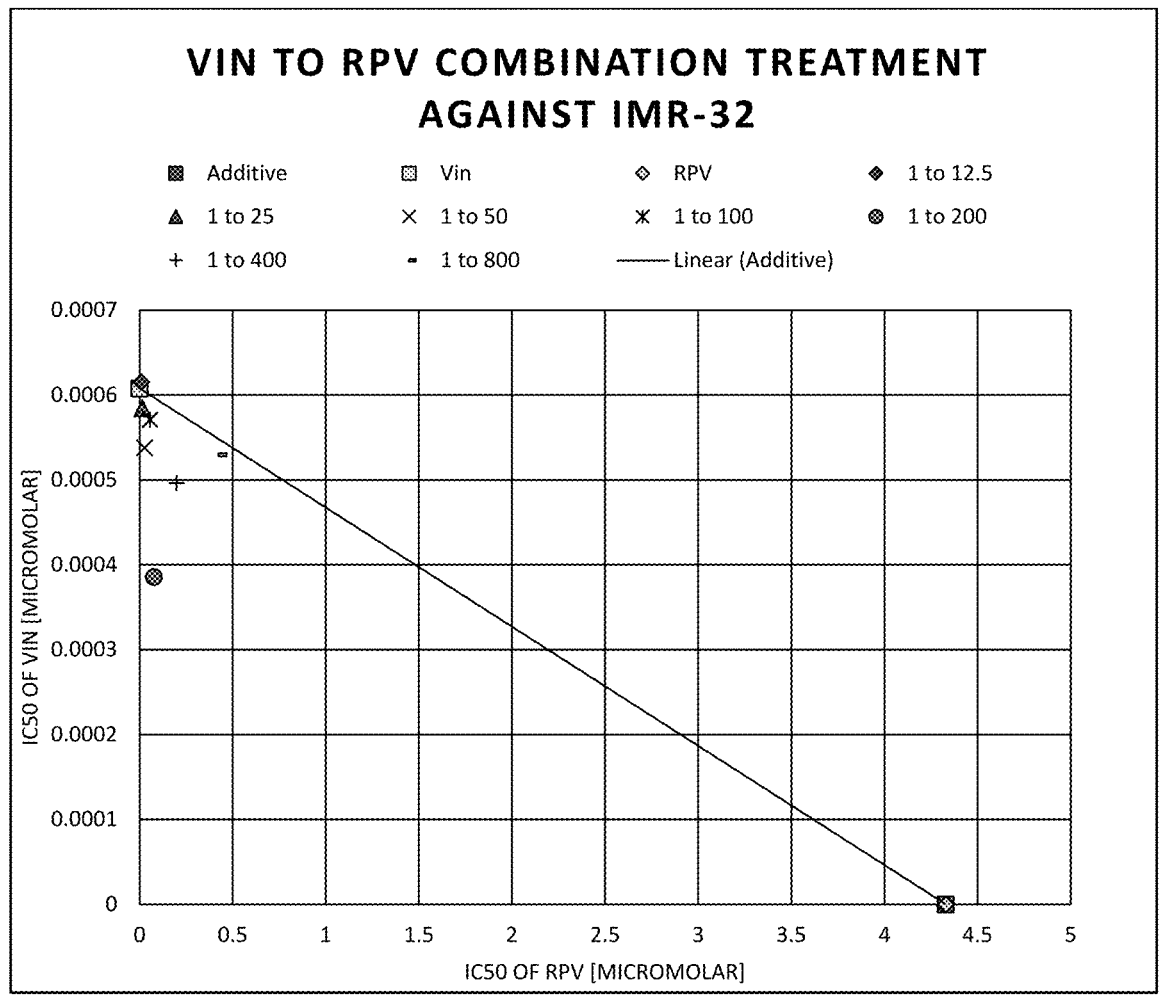
FIG. 19 presents the isobologram analysis of the combination treatment vincristine (Vin) and of rilpivirine (RPV) against IMR-32 cell line.
Figure 20:
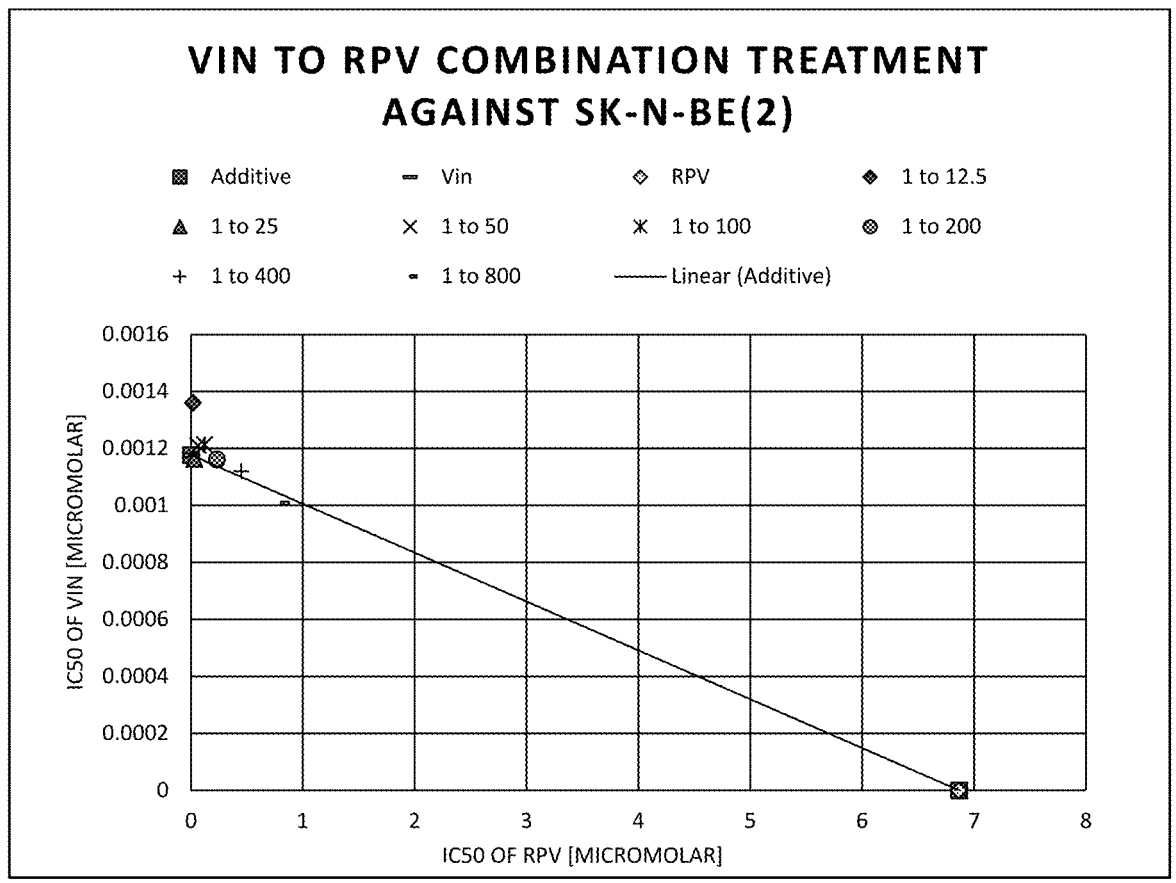
FIG. 20 presents the isobologram analysis of the combination treatment vincristine (Vin) and of rilpivirine (RPV) against SK-N-BE(2) cell line.
Figure 21:
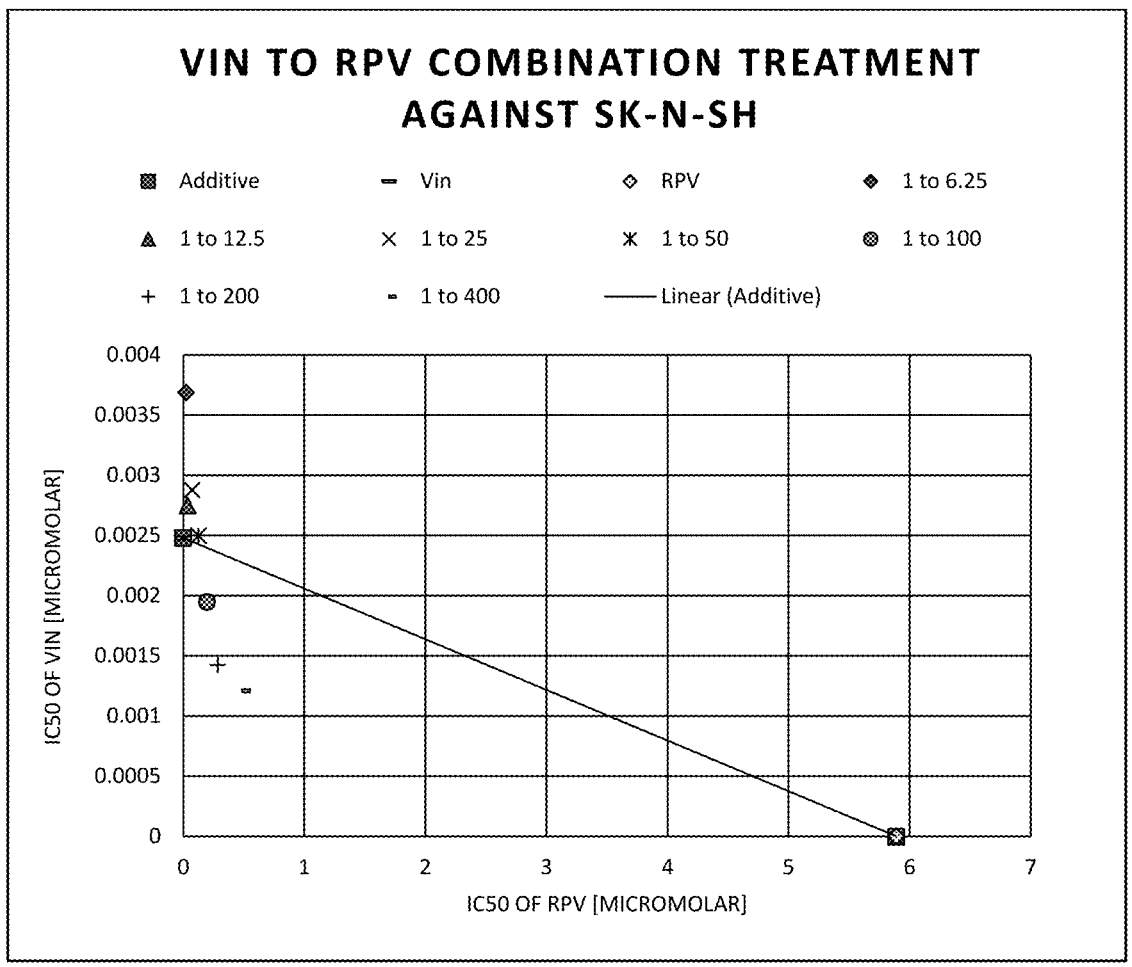
FIG. 21 presents the isobologram analysis of the combination treatment vincristine (Vin) and of rilpivirine (RPV) against SK-N-SH cell line.

Vincristine (Vin) is a chemotherapy medication used for cancer treatment including acute lymphocytic leukemia, acute myeloid leukemia, Hodgkin's disease, neuroblastoma, and small cell lung cancer. Isobologram analysis shows synergistic effects with different ratios of rilpivirine and Vin against SH-SY5Y cell line (FIG. 18) and the combination index analysis also shows synergistic effect that the CI is less than 1 (Table 18). As for IMR-32 cell line and SK-N-BE(2) cell line, there exists additivity effects in isobologram analysis (FIG. 19 and FIG. 20) and the CI is approximately close to 1 (Table 19 and Table 20). Further, as for SK-N-SH cell line, there exists multiple effects in different combination ratios in isobologram analysis (FIG. 21) and CI is between 0.5 to 1.5 (Table 21).

TABLE 18

Combination index of vincristine (Vin) to rilpivirine (RPV) combination treatment against SH-SY5Y cell line

| Drug concentration ratio [μM (micromolar)] | | Combination Index |
|---|---|---|
| Vin | RPV | |
| 1 | 6.25 | 0.914 |
| 1 | 12.5 | 0.756 |
| 1 | 25 | 0.637 |
| 1 | 50 | 0.657 |
| 1 | 100 | 0.527 |
| 1 | 200 | 0.371 |
| 1 | 400 | 0.373 |

TABLE 19

Combination index of vincristine (Vin) to rilpivirine (RPV) combination treatment against IMR-32 cell line

| Drug concentration ratio [μM (micromolar)] | | Combination Index |
|---|---|---|
| Vin | RPV | |
| 1 | 12.5 | 1.014 |
| 1 | 25 | 0.965 |
| 1 | 50 | 0.891 |
| 1 | 100 | 0.953 |
| 1 | 200 | 0.652 |

TABLE 19-continued

Combination index of vincristine (Vin)
to rilpivirine (RPV) combination treatment
against IMR-32 cell line

| Drug concentration ratio [μM (micromolar)] | | Combination Index |
|---|---|---|
| Vin | RPV | |
| 1 | 400 | 0.862 |
| 1 | 800 | 0.969 |

TABLE 20

Combination index of vincristine (Vin)
to rilpivirine (RPV) combination treatment
against SK-N-BE(2) cell line

| Drug concentration ratio [μM (micromolar)] | | Combination Index |
|---|---|---|
| Vin | RPV | |
| 1 | 12.5 | 1.158 |
| 1 | 25 | 0.992 |
| 1 | 50 | 1.037 |
| 1 | 100 | 1.048 |
| 1 | 200 | 1.020 |
| 1 | 400 | 1.017 |
| 1 | 800 | 0.973 |

TABLE 21

Combination index of vincristine (Vin)
to rilpivirine (RPV) combination treatment
against SK-N-SH cell line

| Drug concentration ratio [μM (micromolar)] | | Combination Index |
|---|---|---|
| Vin | RPV | |
| 1 | 6.25 | 1.492 |
| 1 | 12.5 | 1.115 |
| 1 | 25 | 1.174 |
| 1 | 50 | 1.029 |
| 1 | 100 | 0.819 |
| 1 | 200 | 0.623 |
| 1 | 400 | 0.571 |

Example 7 (In Vitro Data of Rilpivirine in Combination with Carboplatin Against Multiple Neuroblastoma Cell Lines)

Figure 22:
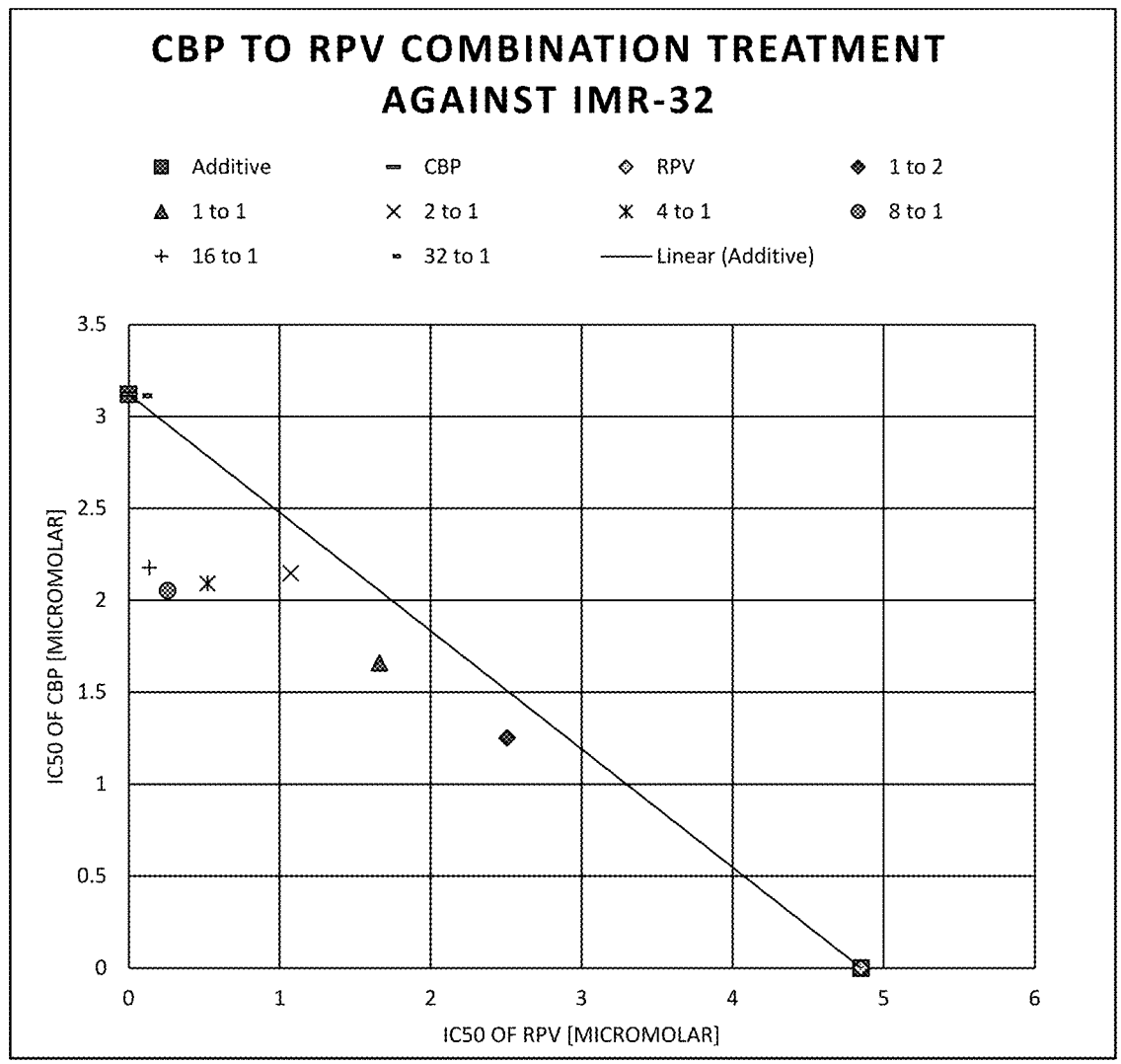
FIG. 22 presents the isobologram analysis of the combination treatment carboplatin (CBP) and of rilpivirine (RPV) against IMR-32 cell line.
Figure 23:
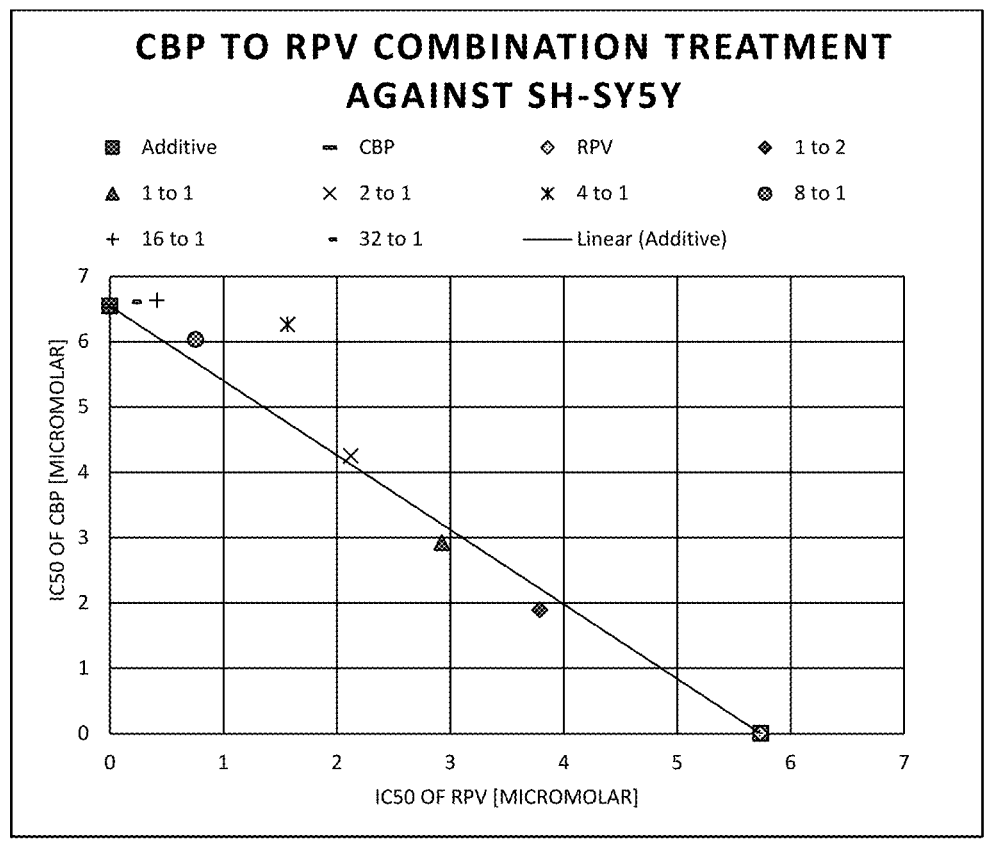
FIG. 23 presents the isobologram analysis of the combination treatment carboplatin (CBP) and of rilpivirine (RPV) against SH-SY5Y cell line.
Figure 24:
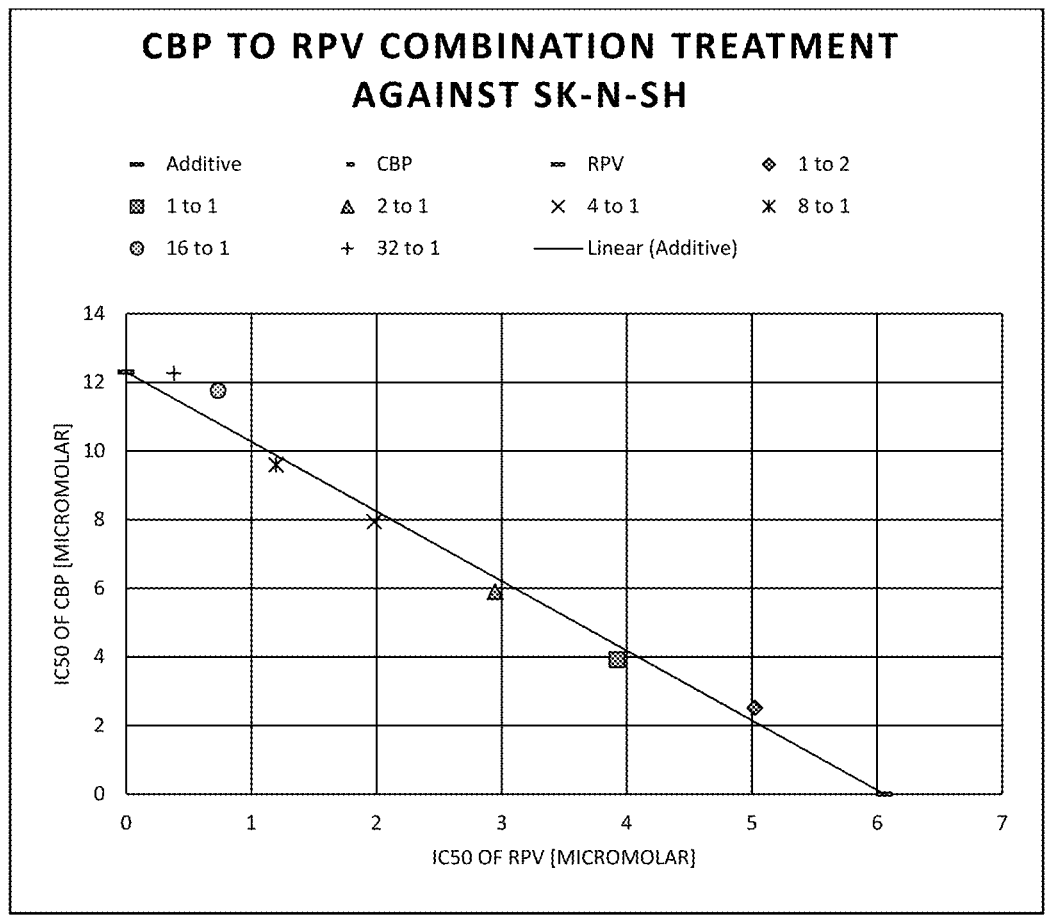
FIG. 24 presents the isobologram analysis of the combination treatment carboplatin (CBP) and of rilpivirine (RPV) against SK-N-SH cell line.
Figure 25:
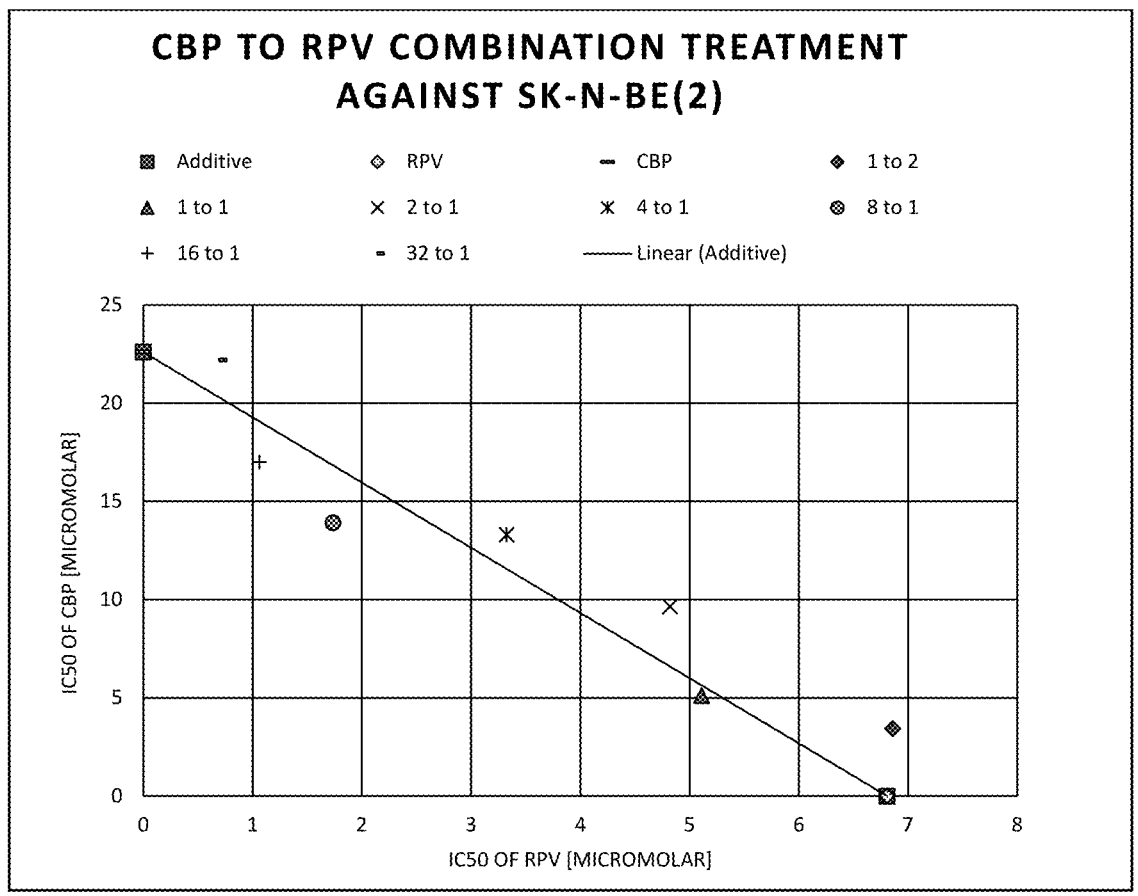
FIG. 25 presents the isobologram analysis of the combination treatment carboplatin (CBP) and of rilpivirine (RPV) against SK-N-BE(2) cell line.

Carboplatin (CBP) is a chemotherapy medication used for cancer treatment including ovarian cancer, lung cancer, head and neck cancer, brain cancer, and neuroblastoma. The isobologram analysis shows mild synergistic effects with different combinations of rilpivirine and Vin against IMR-32 cell line (FIG. 22) and the combination index analysis also shows synergistic effect that the CI is less than 1 (Table 22). As for SH-SY5Y cell line and SK-N-SH cell line, it shows additivity effects in isobologram analysis (FIG. 23 and FIG. 24) and the CI is approximately close to 1 (Table 23 and Table 24). Further, as for SK-N-BE(2) cell line, it shows antagonist effects in isobologram analysis (FIG. 25) and CI is over 1.3 (Table 25).

TABLE 22

Combination index of carboplatin (CBP)
to rilpivirine (RPV) combination treatment
against IMR-32 cell line

| Drug concentration ratio [μM (micromolar)] | | Combination Index |
|---|---|---|
| CBP | RPV | |
| 1 | 2 | 0.918 |
| 1 | 1 | 0.874 |
| 2 | 1 | 0.909 |
| 4 | 1 | 0.778 |
| 8 | 1 | 0.711 |
| 16 | 1 | 0.726 |
| 32 | 1 | 1.018 |

TABLE 23

Combination index of carboplatin (CBP)
to rilpivirine (RPV) combination treatment
against SH-SY5Y cell line

| Drug concentration ratio [μM (micromolar)] | | Combination Index |
|---|---|---|
| CBP | RPV | |
| 1 | 2 | 0.950 |
| 1 | 1 | 0.957 |
| 2 | 1 | 1.019 |
| 4 | 1 | 1.230 |
| 8 | 1 | 1.053 |
| 16 | 1 | 1.086 |
| 32 | 1 | 1.046 |

TABLE 24

Combination index of carboplatin (CBP)
to rilpivirine (RPV) combination treatment
against SK-N-SH cell line

| Drug concentration ratio [μM (micromolar)] | | Combination Index |
|---|---|---|
| CBP | RPV | |
| 1 | 2 | 1.033 |
| 1 | 1 | 0.966 |
| 2 | 1 | 0.966 |
| 4 | 1 | 0.973 |
| 8 | 1 | 0.978 |
| 16 | 1 | 1.077 |
| 32 | 1 | 1.061 |

TABLE 25

Combination index of carboplatin (CBP)
to rilpivirine (RPV) combination treatment
against SK-N-BE(2) cell line

| Drug concentration ratio [μM (micromolar)] | | Combination Index |
|---|---|---|
| CBP | RPV | |
| 1 | 2 | 1.159 |
| 1 | 1 | 0.976 |
| 2 | 1 | 1.134 |

TABLE 25-continued

Combination index of carboplatin (CBP)
to rilpivirine (RPV) combination treatment
against SK-N-BE(2) cell line

| Drug concentration ratio [μM (micromolar)] | | Combination Index |
|---|---|---|
| CBP | RPV | |
| 4 | 1 | 1.077 |
| 8 | 1 | 0.870 |
| 16 | 1 | 0.908 |
| 32 | 1 | 1.084 |

Example 8 (In Vitro Data of Rilpivirine Alone Against Other Cancer Cell Lines)

In addition to neuroblastoma cell lines, the potency of rilpivirine alone has also been shown in other cancer cell lines (Table 26).

TABLE 26

$EC_{50}$ values of each cancer cell lines applied with rilpivirine alone.

| Tumor sub-type | Cell Line | EC50 (uM) |
|---|---|---|
| Acute lymphoblastic leukemia | MOLT-16 | 3.38 |
| Acute lymphoblastic leukemia | Jurkat | 3.68 |
| Acute lymphoblastic leukemia | MOLT-4 | 3.75 |
| Acute lymphoblastic leukemia | CEM-C2 | 4.04 |
| Acute monocytic leukemia | Thp1 | 4.29 |
| Acute T-cell leukemia | J-RT3-T3-5 | 4.04 |
| Biphenotypic B myelomonocytic leukemia | MV-4-11 | 4.88 |
| B-cell non-Hodgkin lymphoma | SU-DHL-4 | 4.29 |
| B-cell precursor leukemia (CML) | BV-173 | 3.69 |
| Bladder | 647-V | 12.3 |
| Breast | T47D | 3.23 |
| Burkitt's lymphoma | Daudi | 4.01 |
| Burkitt's lymphoma | EB2 | 4.81 |
| Burkitt's lymphoma | GA-10 | 3.70 |
| Burkitt's lymphoma | ST486 | 3.76 |
| B-cell lymphoma | DOHH-2 | 4.45 |
| Chronic myelogenous leukemia | EM-2 | 3.96 |
| Chronic myelogenous leukemia | KU812 | 4.09 |
| Colon | RKO-AS45-1 | 4.40 |
| Duodenum | HuTu80 | 3.59 |
| Erythroleukemia | TF-1 | 3.76 |
| Glioblastoma/malignant glioma | U-87 MG | 14.4 |
| Histiocytic lymphoma | TUR | 2.08 |
| Histiocytic lymphoma | U-937 | 3.37 |
| Kidney | Caki-2 | 4.05 |
| Large cell lymphoma | SU-DHL-8 | 4.19 |
| Large cell immunoblastic lymphoma | SR | 3.78 |
| Liver | HUH-6 | 2.41 |
| Mantle cell lymphoma | JVM-2 | 2.74 |
| Medulloblastoma | D283Med | 3.54 |
| Melanoma | HMCB | 3.49 |
| Multiple myeloma | IM-9 | 4.13 |
| NSCLC | COR-L105 | 3.11 |
| Neuroblastoma | CHP-212 | 3.26 |
| Neuroblastoma | SK-N-AS | 4.84 |
| Pancreas | BxPC-3 | 11.3 |
| Pancreas | PANC-1 | 8.27 |
| Prostate | PC-3 | 6.23 |
| SCLC | DMS273 | 4.96 |
| Stomach | SNU-16 | 4.23 |
| Uterine sarcoma | MES-SA | 4.91 |

Figure 26:
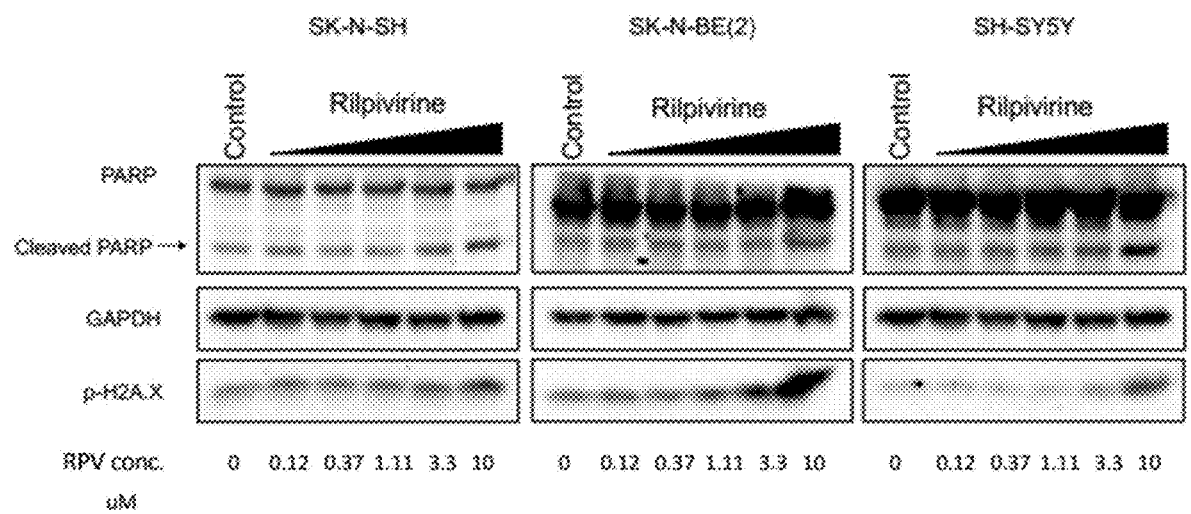
FIG. 26 illustrates the expressions of cleaved PARP and p-H2A.X in neuroblastoma cell lines SK-N-SH, SK-N-BE (2) and SH-SY5Y after applying different concentrations of rilpivirine.
Figure 27:
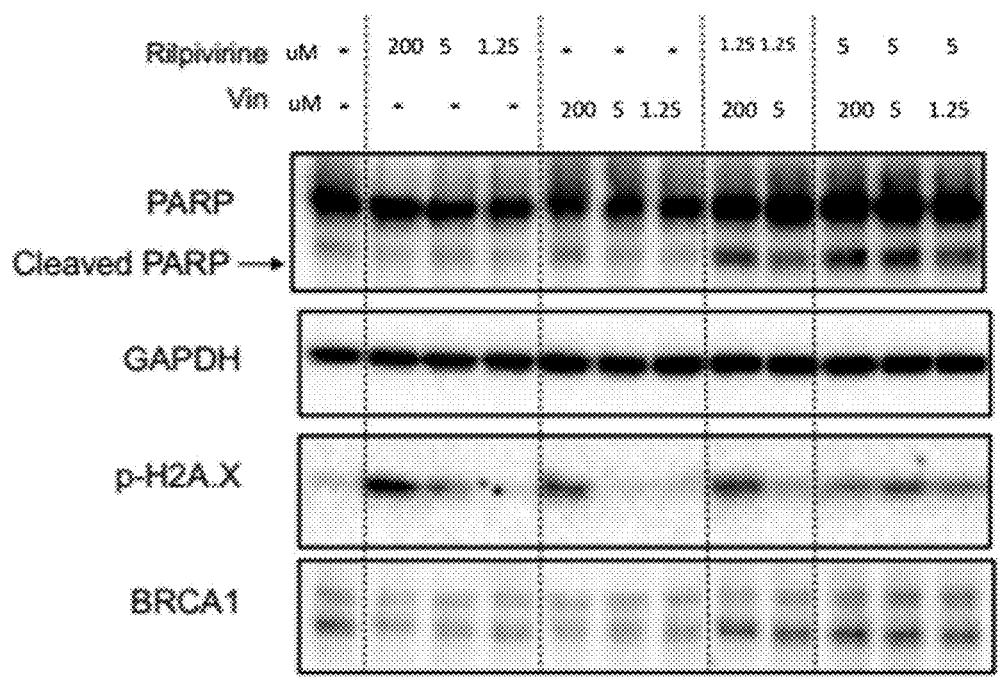
FIG. 27 illustrates the expressions of cleaved PARP, p-H2A.X and BRCA1 in neuroblastoma cell lines IMR-32 after applying different concentrations of rilpivirine, vincristine and rilpivirine plus vincristine.

Referring to FIG. 26, by increasing the concentrations of rilpivirine (0.12, 0.37, 1.11, 3.3, and 10 μM) applied on SK-N-SH, SK-N-BE(2) and SH-SY5Y neuroblastoma cell lines, the expression of cleaved poly (ADP-ribose) polymerase (PARP) and phosphor-histone H2A.X (p-H2A.X) increased gradually, suggesting rilpivirine alone can cause DNA damage and lead to cell apoptosis of neuroblastoma or other cancer cells. Furthermore, comparing to single drug treatments, combinations of rilpivirine with chemotherapy drug vincristine showed increased expressions of cleaved PARP and P-H2A.X, suggesting an enhancement on DNA damage and cell apoptosis in neuroblastoma cell line IMR-32, in addition, and tumor suppressor gene BRCA1 was also upregulated. (FIG. 27).

In Vivo Analysis

In the present invention, rilpivirine was used alone or in combination with chemotherapy drugs such as cisplatin, carboplatin, and vincristine, to evaluate the treatment efficacy in a xenograft mouse model of neuroblastoma. Please refer to the Xenograft Mouse Model section above for the details of the in vivo tests.

Example 9 (In Vivo Data of Rilpivirine with Cisplatin on Mouse Model)

Figure 28:
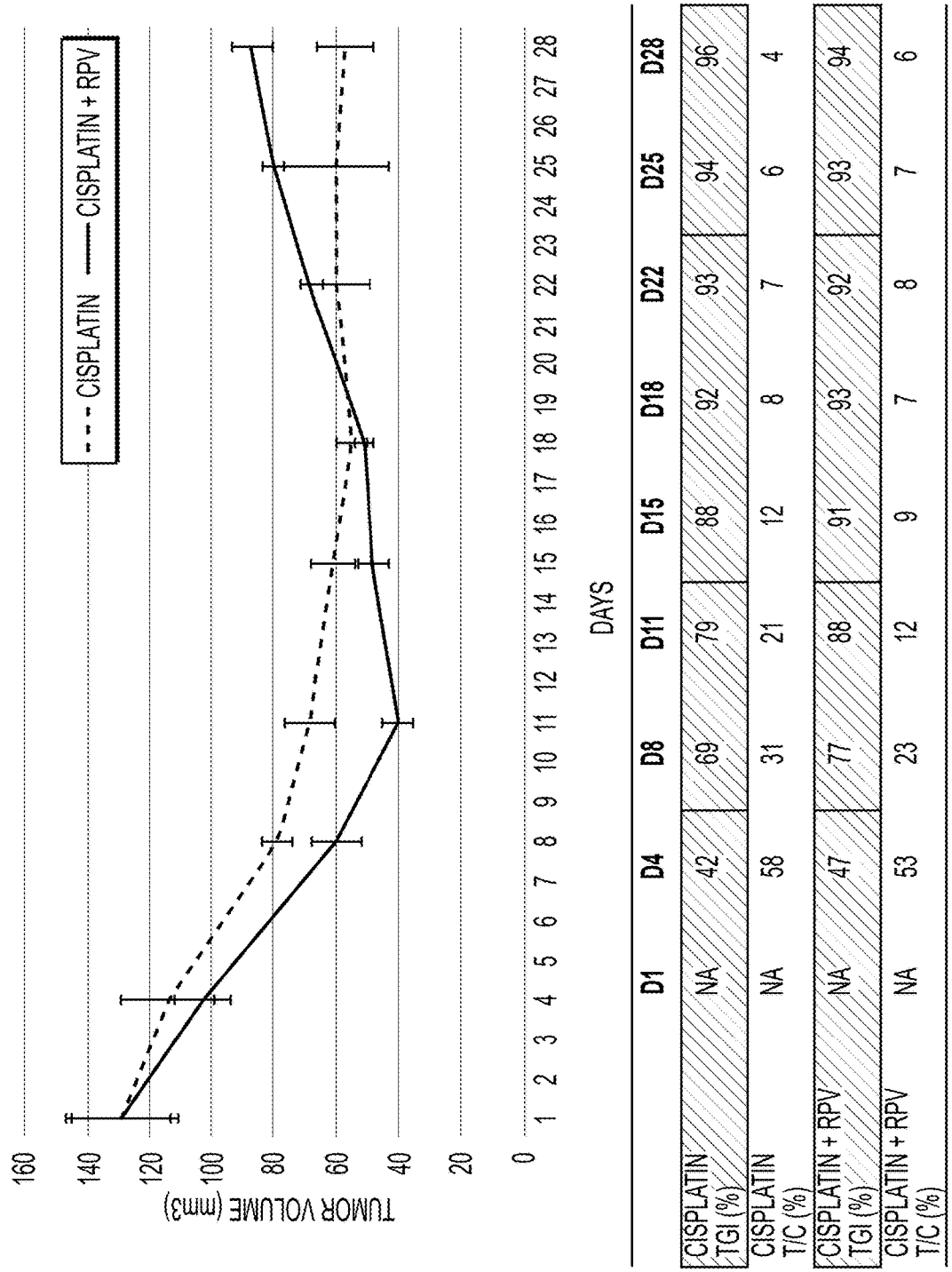
FIG. 28 illustrates volume changes of the neuroblastoma tumor after the administration of the cisplatin and cisplatin with rilpivirine in an animal model.

As shown in FIG. 28, the tumor volume resulting from the combination therapy comprising intraperitoneal injection of cisplatin at 7 mg/kg on Day 1 and oral administration of rilpivirine at 400 mg/kg once daily for 21 consecutive days was smaller than that of the monotherapy group comprising intraperitoneal injection of cisplatin at 7 mg/kg weekly for three weeks, especially on Day 11, in a statistically significant manner (unpaired student's t-test, p<0.05), wherein the tumor growth inhibition is approximately over 88%. The maximum % TGI values of approximately 94% appears to be on Day 28.

Example 10 (In Vivo Data of Rilpivirine with Carboplatin on Mouse Model)

Figure 29:
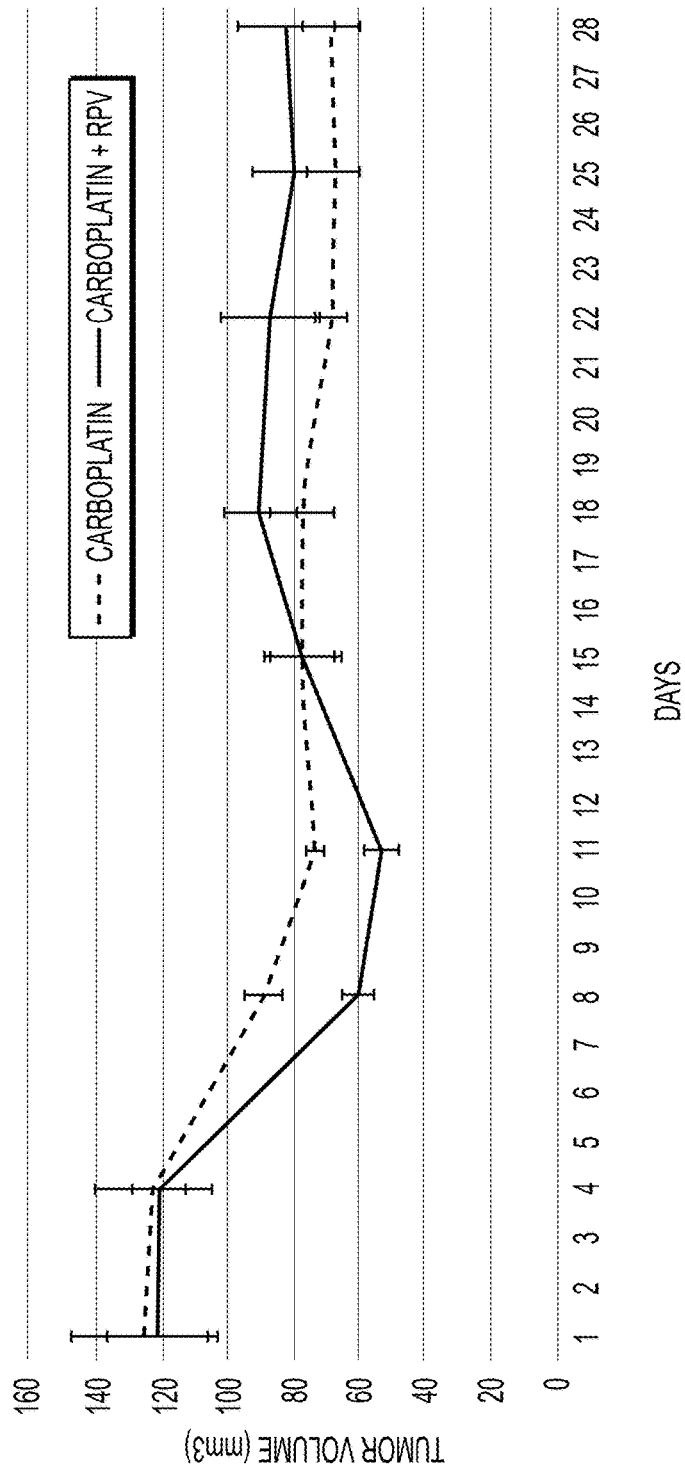
FIG. 29 illustrates volume changes of the neuroblastoma tumor after the administration of the carboplatin and carboplatin with rilpivirine in an animal model.

Further, as shown in FIG. 29, the tumor volume resulting from the combination therapy comprising intraperitoneal injection of carboplatin at 80 mg/kg on Day 1 and oral administration of rilpivirine at 400 mg/kg daily (QD×11) was smaller than that of the monotherapy group comprising intraperitoneal injection of carboplatin at 80 mg/kg weekly for three weeks, especially on Day 8 and Day 11, in a statistically significant manner (unpaired student's t-test, p<0.05), wherein the tumor growth inhibition is approximately over 77% and 84%. The maximum % TGI values of approximately 94% appears to be on Day 28.

Example 11 (In Vivo Data of Rilpivirine with Vincristine on Mouse Model)

Figure 30:
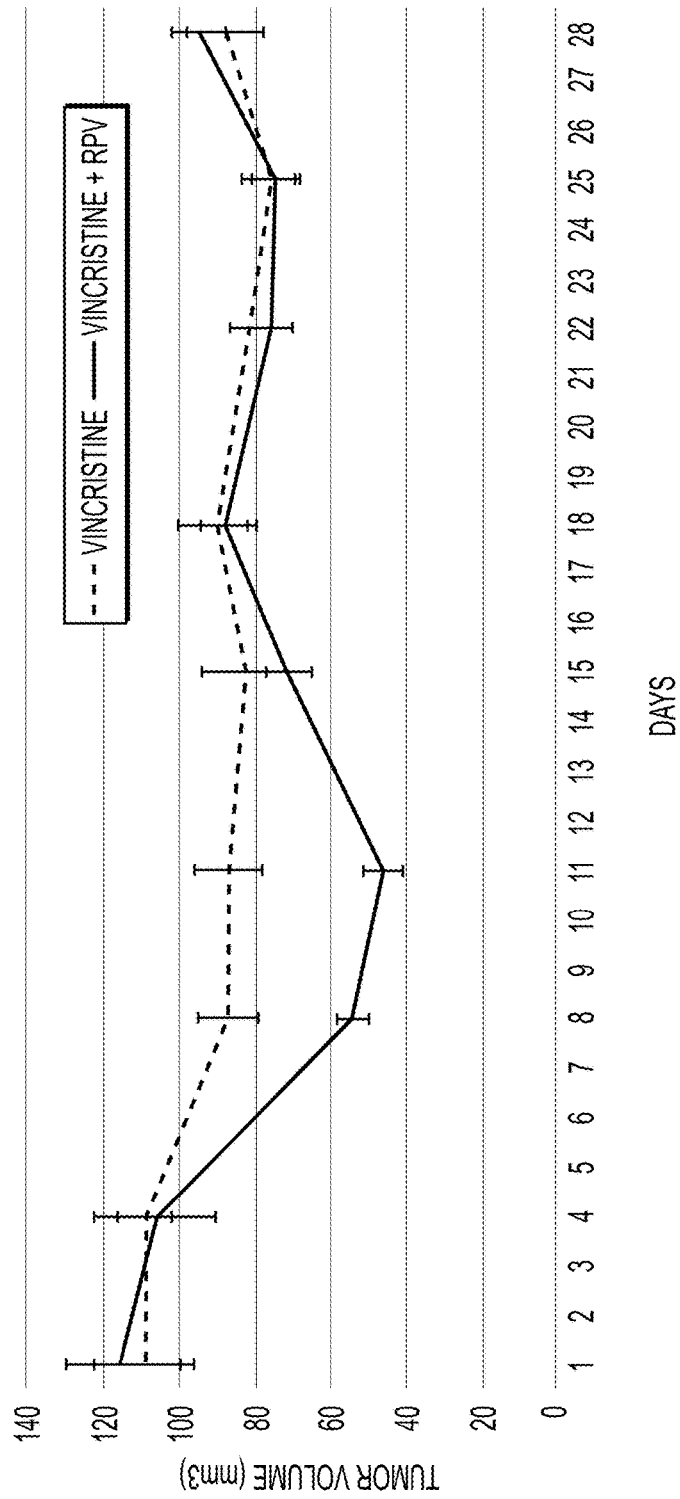
FIG. 30 illustrates volume changes of the neuroblastoma tumor after the administration of the vincristine and vincristine with rilpivirine in an animal model.
Figure 31:
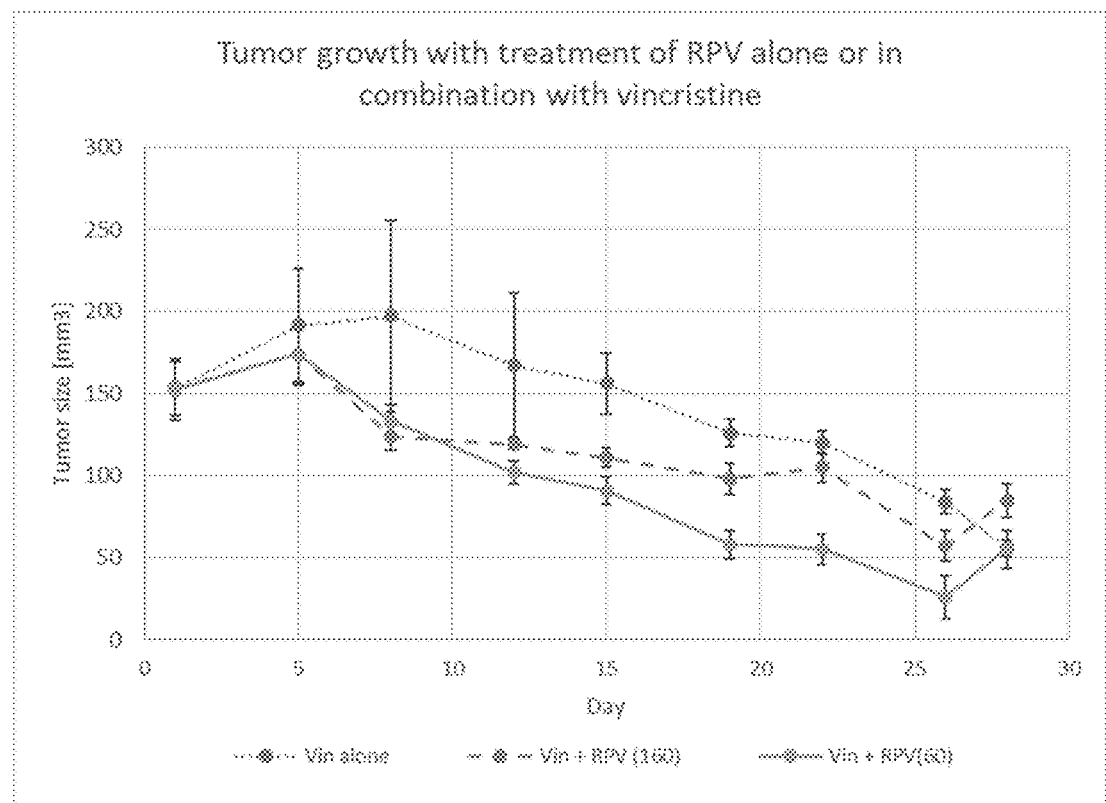
FIG. 31 illustrates volume changes of the neuroblastoma tumor after the administration of the vincristine alone and vincristine with different concentrations of rilpivirine (60 mg and 160 mg respectively) in an animal model.

Further, as shown in FIG. 30, the tumor volume resulting from the combination therapy comprising intraperitoneal injection of vincristine at 1 mg/kg on Day 1 and oral administration of rilpivirine at 400 mg/kg daily (QD×11) was smaller than that of the monotherapy group comprising intraperitoneal injection of vincristine at 1 mg/kg weekly for three weeks, especially on Day 8 and Day 11, in a statistically significant manner (unpaired t-test, p<0.05), wherein the tumor growth inhibition is approximately over 86%. The maximum % TGI values of approximately 93% appears to be on Day 28.

It is worth noting that the chemotherapy drugs in the combination therapy groups (in Examples 9-11) were applied on Day 1 only, and as for the monotherapy groups, the chemotherapy drugs were applied on Day 1, Day 8 and Day 15. This indicates that administration of rilpivirine could reduce the dosage frequency or amount of cytotoxic chemotherapy drugs, thus potentially ameliorating the side-effects caused by the chemotherapy drugs. The dosage frequency was approximately reduced from thrice a month to once a month or twice a week to once a week.

In another embodiment, the intraperitoneal injection of carboplatin or vincristine combination therapy with rilpivirine, all drug treatment was stopped after Day 11, and the tumor volume was not statistically different from the monotherapy groups, suggesting long-term inhibition effect of rilpivirine.

The above in vivo combination studies were performed to elucidate the influence of rilpivirine on rapid COJEC, one of the standard regimens for the treatment of high-risk neuroblastoma patients. Rilpivirine was combined with each chemotherapy drug in rapid COJEC (includes cisplatin, carboplatin, vincristine, cyclophosphamide and etoposide) and the potential benefit was assessed in a xenograft mouse model.

Based on the data from this in vivo study, rilpivirine potentiated the efficacy of cisplatin, carboplatin and vincristine against the neuroblastoma xenograft model. Generally speaking, combination therapy brought a statistically significant reduction in the tumor volume (unpaired student's t-test, $p<0.05$) compared to that of the monotherapy groups on Day 8 and 11 for carboplatin and vincristine and Day 11 for cisplatin. It is worth noting that the chemotherapeutic drugs in the combination therapy groups were dosed on Day 1 only. Meanwhile, in the monotherapy groups, the chemotherapeutic drugs were dosed on Day 1, Day 8 and Day 15. This may indicate that rilpivirine could reduce the dosing frequency of cytotoxic chemotherapeutic drugs.

In addition, rilpivirine+cisplatin group was observed to achieve similar tumor size (unpaired student's t-test, $p>0.05$) compared with the cisplatin alone group from Day 11 to 15 and no difference until Day 25. For the carboplatin and vincristine combination groups, we stopped the treatment on Day 11 but the tumor size was not statistically different from the chemo alone groups.

On the other hand, we also observed that rilpivirine did not interfere or weaken the therapeutic effect of cyclophosphamide and etoposide in the xenograft model. There was no significant difference in the tumor size between the monotherapy and the combination therapy in the 28-day in vivo studies which compared cyclophosphamide alone against cyclophosphamide+rilpivirine and etoposide alone against etoposide+rilpivirine, respectively.

Based on this in vivo study, rilpivirine was found to potentiate the therapeutic effects of cisplatin, carboplatin and vincristine and potentially reduce the dosing frequency of the cytotoxic chemotherapy drugs during the treatment of neuroblastoma. On the other hand, rilpivirine did not weaken the therapeutic effects of cyclophosphamide and etoposide. Therefore, superiority and improvement may be observed by incorporating rilpivirine with standard chemotherapy against neuroblastoma.

Example 12 (In Vivo Data of Rilpivirine Alone on Mouse Model)

Figure 32:
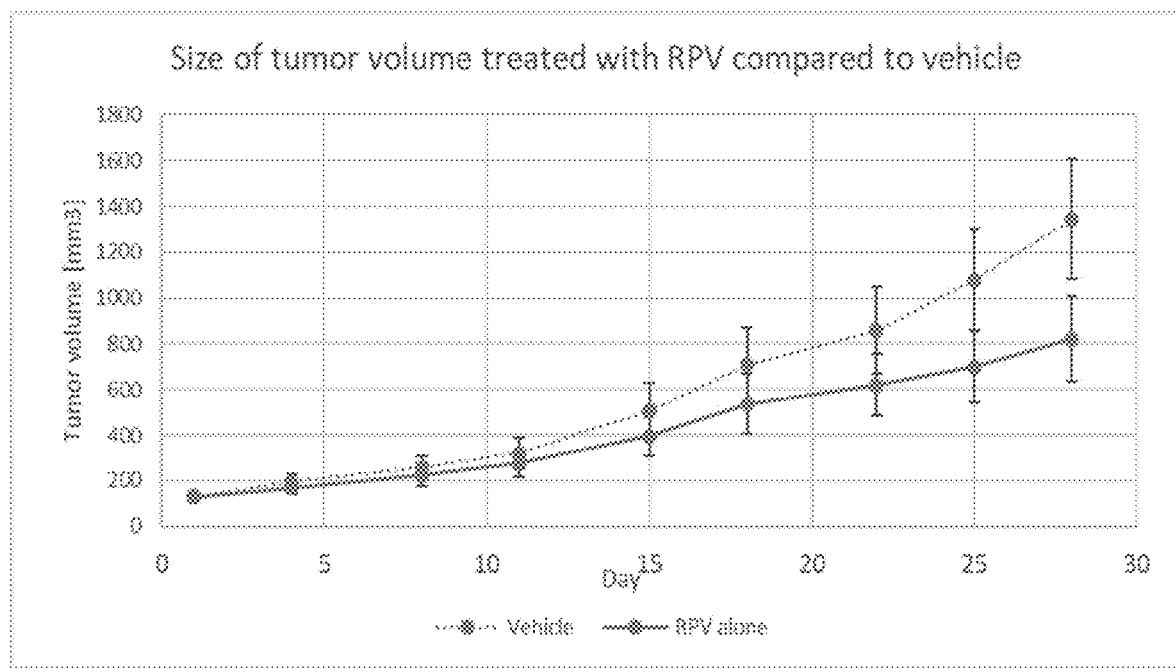
FIG. 32 illustrates volume changes of the neuroblastoma tumor after the administration of rilpivirine only in an animal model.

As shown in FIG. 32, compared to the negative control group administering vehicle (0.5% HPMC) once daily for 21 consecutive days via oral administration, tumor growth was significantly inhibited in the group administering rilpivirine 400 mg/kg once daily for 21 consecutive days via oral administration (unpaired student's t-test, $p<0.05$), indicating anti-tumor activity of rilpivirine alone against neuroblastoma. During the course of the administration, rilpivirine was well tolerated and not associated with body weight loss and no overt toxicities were observed.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the methods of preparation described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated. Furthermore, specified steps can be carried out concurrently unless explicit claim language recites that they be carried out separately.

Definitions for selected terms used herein may be found within the detailed description of the present invention and apply throughout. Unless otherwise defined, all other technical terms used herein have the same meaning as commonly understood to one of ordinary skill in the art to which the present invention belongs.

It will be appreciated by those skilled in the art, in view of these teachings, that alternative embodiments may be implemented without deviating from the spirit or scope of the invention, as set forth in the appended claims. This invention is to be limited only by the following claims, which include all such embodiments and modifications when viewed in conjunction with the above specification and accompanying drawings.

The invention claimed is:

1. A method for preventing growth of and/or treating a cancerous tumor and/or delaying onset of cancer from tumor-initiating cells, the method comprising:

administering a composition comprising an effective amount of a compound of Formula (I) or Formula (II):

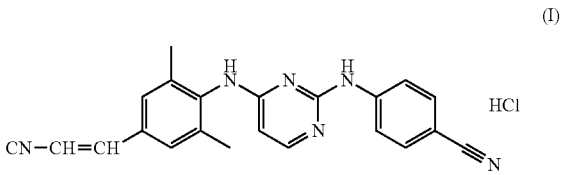

(I)

-continued

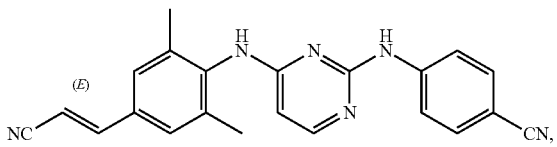

(II)

or any pharmaceutically acceptable salt thereof, to a subject in need thereof, wherein the effective amount of said compound in the composition is from 1 mg to 25 mg per day.

2. The method of claim 1, wherein the cancerous tumor or cancer comprises a mastocytoma or a mast cell tumor, an ovarian cancer, a non-small cell lung cancer, small cell lung cancer, hepatocarcinoma, melanoma, retinoblastoma, breast tumor, colorectal carcinoma, leukemia, lymphoma, acute lymphoblastic leukemia (ALL) or acute lymphoid leukemia, acute myeloid leukemia (AML), a histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer.

3. The method of claim 2, wherein the cancerous tumor or cancer comprises neuroblastoma.

4. The method of claim 1, wherein said subject is a human comprising adult, juvenile, children or infants.

5. The method of claim 1, wherein the composition is administered at least once daily.

6. The method of claim 1, wherein the administering a composition of Formula (I) is in combination with one or more chemotherapeutic agents, biological agents and/or anticancer agents, to a subject in need thereof.

7. The method of claim 6 wherein the one or more chemotherapeutic agents comprises one or more alkylating agents, anti-metabolites, antitumor antibiotics, topoisomerase inhibitors, mitotic inhibitors, steroids, and/or any mixtures thereof; and the one or more biological agents comprises one or more vaccines, cytokines, antibodies, protein and peptide drugs and/or any mixtures thereof.

8. The method of claim 7, wherein said alkylating agents are one or more selected from cyclophosphamide, melphalan, temozolomide, carboplatin, cisplatin, and/or oxaliplatin.

9. The method of claim 7, wherein said anti-metabolites are one or more selected from 5-fluorouracil, 6-mercaptopurine, cytarabine, gemcitabine, and/or methotrexate.

10. The method of claim 7, wherein said antitumor antibiotics are one or more selected from actinomycin-D, bleomycin, daunorubicin, and/or doxorubicin.

11. The method of claim 7, wherein said topoisomerase inhibitors are one or more selected from etoposide, irinotecan, teniposide, and/or topotecan.

12. The method of claim 7, wherein said mitotic inhibitors are one or more selected from docetaxel, estramustine, paclitaxel, and/or vinblastine.

13. The method of claim 7, wherein said steroids are one or more selected from prednisone, methylprednisolone, and/or dexamethasone.

14. The method of claim 7, wherein said antibodies are selected from Hu3F8, hu14.18K322A, Hu14.18-IL-2, dinutuximab or any combination thereof.

15. A composition for preventing growth of and/or treating a cancerous tumor and/or delaying onset of cancer from tumor-initiating cells, the composition comprising:

an effective amount of a compound of Formula (I) or Formula (II):

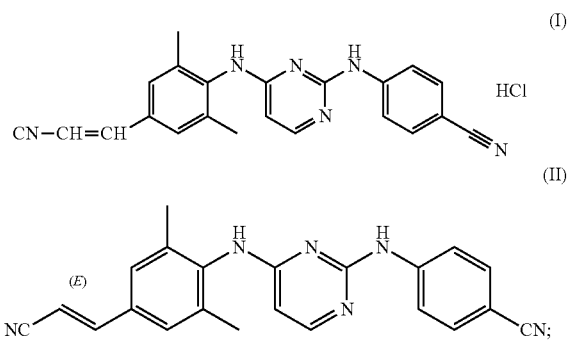

or any pharmaceutically acceptable salt thereof, the composition further including one or more antitumor antibiotics selected from actinomycin-D, bleomycin, daunorubicin, and/or doxorubicin;

topoisomerase inhibitors selected from etoposide, irinotecan, teniposide, and/or topotecan;

mitotic inhibitors selected from docetaxel, estramustine, paclitaxel, and/or vinblastine;

steroids selected from prednisone, methylprednisolone, and/or dexamethasone; or antibodies selected from Hu3F8, hu14.18K322A, Hu14.18-IL-2, dinutuximab or any combination thereof.

16. The composition of claim 15, wherein said composition is formulated into one or more of the following administrative forms: a parenteral formulation, an aqueous solution, a liposome, an injectable solution, an injectable suspension, an intravenous solution, an intravenous suspension/nanosuspension, a tablet, a pill, a lozenge, a capsule, a caplet, a patch, a spray, an inhalant, a powder, a freeze-dried powder, a patch, a gel, a geltab, a suspension, a nanosuspension, a microparticle, a nanoparticle, a nanoliposome, a microgel, a pellet, a suppository, an oral suspension, an oral disintegrating tablet, an oral dispersible tablet, an oral disintegrating film, a microemulsion, a nanoemulsion and a self-emulsifying drug delivery system and/or any combination thereof.

17. A method for reducing the frequency or amount of a chemotherapeutic agent needed to treat a cancerous tumor and/or delay progression of cancer from tumor-initiating cells, the method comprising:

administering a composition comprising an effective amount of a compound of Formula (I) or Formula (II):

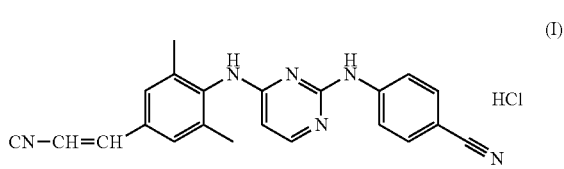

-continued (II)

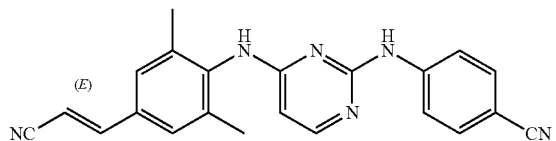

or any pharmaceutically acceptable salt thereof, in combination with one or more of chemotherapeutic agents, to a subject in need thereof,
the one or more of the chemotherapeutic agents being selected from alkylating agents, anti-metabolites, antitumor antibiotics, topoisomerase inhibitors, mitotic inhibitors, steroids and/or any mixtures thereof;
wherein the frequency or amount of the chemotherapeutic agent administered is approximately up to 75 to 90 percent less than a standard protocol without administration of the composition comprising an effective amount of the compound of Formula (I) or Formula (II).

18. A method for preventing growth of and/or treating a cancerous tumor and/or delaying onset of cancer from tumor-initiating cells, the method comprising:
administering a composition comprising an effective amount of a compound of Formula (I) or Formula (II):

(I)

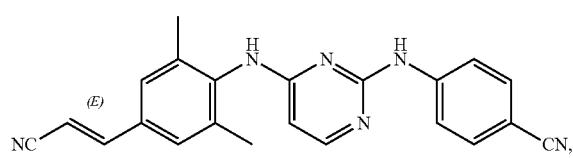 HCl (II)

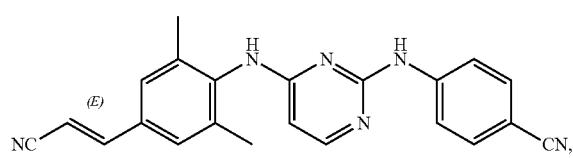

or any pharmaceutically acceptable salt thereof, to a subject in need thereof,
wherein the administering a composition of Formula (I) or Formula (II) is in combination with one or more chemotherapeutic agents or biological agents,
wherein the one or more chemotherapeutic agents are selected from (i) antitumor antibiotics selected from actinomycin-D, bleomycin, daunorubicin, and/or doxorubicin; (ii) topoisomerase inhibitors selected from etoposide, irinotecan, teniposide, and/or topotecan; (iii) mitotic inhibitors selected from docetaxel, estramustine, paclitaxel, and/or vinblastine; (iv) steroids selected from prednisone, methylprednisolone, and/or dexamethasone; and/or (v) any mixtures thereof; and
wherein the one or more biological agents are selected from antibodies selected from Hu3F8, hu14.18K322A, Hu14.18-IL-2, dinutuximab or any combination thereof.

19. The method of claim 18, wherein the cancerous tumor or cancer comprises a mastocytoma or a mast cell tumor, an ovarian cancer, a non-small cell lung cancer, small cell lung cancer, hepatocarcinoma, melanoma, retinoblastoma, breast tumor, colorectal carcinoma, leukemia, lymphoma, acute lymphoblastic leukemia (ALL) or acute lymphoid leukemia, acute myeloid leukemia (AML), a histiocytic sarcoma, a brain tumor, an astrocytoma, a glioblastoma, a neuroma, a neuroblastoma, a colon carcinoma, cervical carcinoma, sarcoma, prostate tumor, bladder tumor, tumor of the reticuloendothelial tissues, Wilm's tumor, ovarian carcinoma, a bone cancer, an osteosarcoma, a renal cancer, or head and neck cancer, oral cancer, a laryngeal cancer, or an oropharyngeal cancer.

20. The method of claim 19, wherein the cancerous tumor or cancer comprises neuroblastoma.

21. The method of claim 18, wherein said subject is a human comprising adult, juvenile, children or infants.

22. The method of claim 18, wherein the effective amount of the compound in the composition is from 0.1 mg to 1000 mg per day.

* * * * *